United States Patent
Amory et al.

(10) Patent No.: US 7,138,389 B2
(45) Date of Patent: Nov. 21, 2006

(54) ORAL ANDROGEN THERAPY USING MODULATORS OF TESTOSTERONE BIOAVAILABILITY

(75) Inventors: John K. Amory, Seattle, WA (US); William J. Bremner, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 10/990,118

(22) Filed: Nov. 15, 2004

(65) Prior Publication Data

US 2005/0176692 A1  Aug. 11, 2005

Related U.S. Application Data

(60) Provisional application No. 60/542,895, filed on Feb. 9, 2004.

(51) Int. Cl.
*A61K 31/56* (2006.01)
(52) U.S. Cl. ....................... 514/171; 514/284
(58) Field of Classification Search ............... 514/171, 514/284
See application file for complete search history.

(56) References Cited

U.S. PATENT DOCUMENTS

| | | | |
|---|---|---|---|
| 4,377,584 A | 3/1983 | Rasmusson et al. | |
| 5,998,427 A | 12/1999 | Batchelor et al. | |
| 6,117,429 A | 9/2000 | Bucci | |
| 6,696,484 B1 | 2/2004 | Liao et al. | |
| 2003/0203043 A1 | 10/2003 | Yegorova | |
| 2004/0110733 A1 | 6/2004 | Borlak et al. | |

FOREIGN PATENT DOCUMENTS

WO  WO 99/65228 A2  12/1999

OTHER PUBLICATIONS

Aakvaag, A. et al. "Plasma Testosterone Values In Different Forms Of Testosterone Treatment." *Acta Endocrinologica* (1969), 60:537-542.

Amory, J.K. et al. "Oral Testosterone-Triglyceride Conjugate in Rabbits: Single-Dose Pharmacokinetics and Comparison With Oral Testosterone Undecanoate." *J Androl.* (Sep./Oct. 2003), 24(5):716-720.

Amory, J.K. et al. "Exogenous Testosterone or Testosterone with Finasteride Increases Bone Mineral Density in Older Men with Low Serum Testosterone." *J Clin Endocrinol & Metab* (2004), 89(2):503-510.

Bagchus, Wilma M. et al. "Important Effect Of Food On The Bioavailability Of Oral Testosterone Undecanoate." *Pharmacotherapy* (Nov. 3, 2003), 23(3):319-325.

Chang, William Y. et al. "Experimentally-Induced Prostatic Hyperplasia in Young Beagles: A Model to Evaluate the Chemotherapeutic Effects of Gossypol." *Res Commun Mol Pathol Pharmacol* (Jun. 1996), 92(3):341-360.

Daggett, P.R. et al. "Oral Testosterone, a Reappraisal." *Hormone Res.* (1978), 9:121-129.

Foss, George L. "Clinical Administration of Androgens, A Comparison of Various Methods." *The Lancet* (Mar. 4, 1939), pp. 502-504.

Franchi, F. et al. "Long-Term Study of Oral Testosterone Undecanoate in Hypogonadal Males." *International Journal of Andrology* (1978), 1:270-278.

Frey, H. et al. "Bioavailability of Oral Testosterone in Males." *European Journal of Clinical Pharmacology* (1979), 16:345-349.

Gormley, Glenn J. et al. "Effects of Finasteride (MK-906), a 5α-Reductase Inhibitor, on Circulating Androgens in Male Volunteers." *Journal of Clinical Endocrinology and Metabolism* (Apr. 1990), 70(4):1136-1141.

Herzog, Andrew G. et al. "Testosterone versus testosterone and testolactone in treating reproductive and sexual dysfunction in men with epilepsy and hypogonadism." *Neurology* (Mar. 1998), 50(3):782-784.

Houwing, Natalie S. et al. "Pharmacokinetic Study in Women of Three Different Doses of a New Formulation of Oral Testosterone Undecanoate, Andriol Testocaps." *Pharmacotherapy* (Nov. 10, 2003), 23(10):1257-1265.

Johnsen, Svend G. et al. "Therapeutic Effectiveness of Oral Testosterone." *The Lancet* (Dec. 21, 1974), pp. 1473-1475.

Kinniburgh, D. et al. "Suppression of Spermatogenesis With Desogestrel and Testosterone Pellets is Not Enhanced by Addition of Finasteride." *J Androl* (Jan.-Feb. 2001), 22(1):88-95.

McLachlan, Robert I. et al. "Efficacy and acceptability of testosterone implants, alone or in combination with a 5α-reductase inhibitor, for male hormonal contraception," *Contraception* (Aug. 2000), 62(2):73-78.

Nieschlag, E. et al. "Plasma Androgen Levels in Men After Oral Administration of Testosterone or Testosterone Undecanoate." *Acta Endocrinologica* (1975), 79:366-374.

Rittmaster, Roger S. "5α-Reductase Inhibitors." *J Androl* (Nov./Dec. 1997), 18(6):582-587.

(Continued)

*Primary Examiner*—Barbara P. Badio
(74) *Attorney, Agent, or Firm*—Townsend and Townsend and Crew LLP

(57) ABSTRACT

This invention provides methods of treating a mammalian subject in need of androgen therapy by orally administering to the subject testosterone, a testosterone ester, or a testosterone precursor in an oil vehicle and by administering to the subject a modulator such as finasteride or dutasteride which increases testosterone bioavailability in the subject.

27 Claims, 14 Drawing Sheets

OTHER PUBLICATIONS

Schürmeyer, E.J. et al. "Saliva and serum testosterone following oral testosterone undecanoate administration in normal and hypogonadal men." *Acta Endocrinologica* (1983), 102:456-462.

Skakkebaek, N.E. et al. "Androgen Replacement With Oral Testosterone Undecanoate In Hypogonadal Men: A Double Blind Controlled Study." *Clinical Endocrinology* (1981), 14:49-61.

Täuber, U., et al. "Absolute bioavailability of testosterone after oral administration of testosterone-undecanoate and testosterone." *European J of Drug Metab & Pharmacokinetics* (1986), 11(2):145-149.

Wright, A.S. et al. "Androgen-Induced Regrowth in the Castrated Rat Ventral Prostrate: Role of 5α-Reductase." *Endocrinology* (1999), 140(10):4509-4515.

Umekita, Yoshihisa et al. "Human prostate tumor growth in athymic mice: inhibition by androgens and stimulation by finasteride." *Proc. Natl. Acad. Sci.* (Oct. 1996), 93:11802-11807.

| Day | Screen | \| 0 | 1 | 2 | 3 | 4 | Treatment Day 5 | 6 | 7 | 8 | 9 | 10 | 11 | Follow-up |
|---|---|---|---|---|---|---|---|---|---|---|---|---|---|---|
| Physical Examination | x | x | | | | | | | | | | | | x |
| Medical History | x | | | | | | | | | | | | | x |
| Baseline testosterone, Chemistry, Hematology, Hepatic Function (once daily) | x | x | x | x | x | x | x | | x | x | x | x | | x |
| Serum testosterone (30 minutes, 1,2,3,4,6,8,10 and 12 hours after dosing-8 draws) | | | x | | x | x | | | | x | | x | | |
| Acyline | | x | | | | | | | | | | | | |
| Oral testosterone (400 mg) | | | x | | x | x | | | | x | | x | | |
| Dutasteride | | | | | | | | | xx | x | x | | | |
| Finasteride | | | | xx | x | x | | | | x | | | | |
| Fasting | | | | x | x | | | | | x | | | | |
| Meal with dose | | x | | | | x | | | | | | x | | |

*Figure 1*

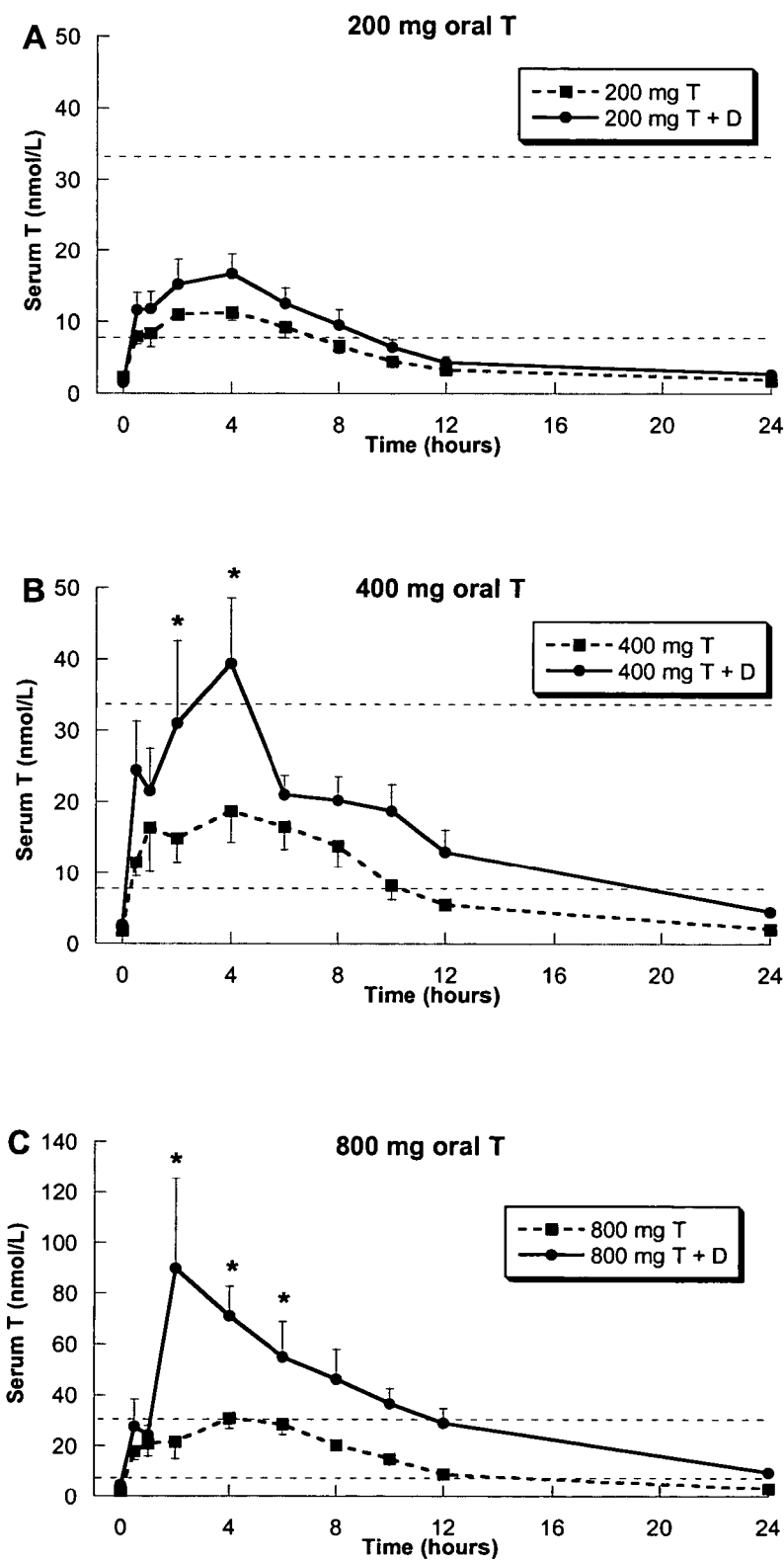
Figure 7A-C

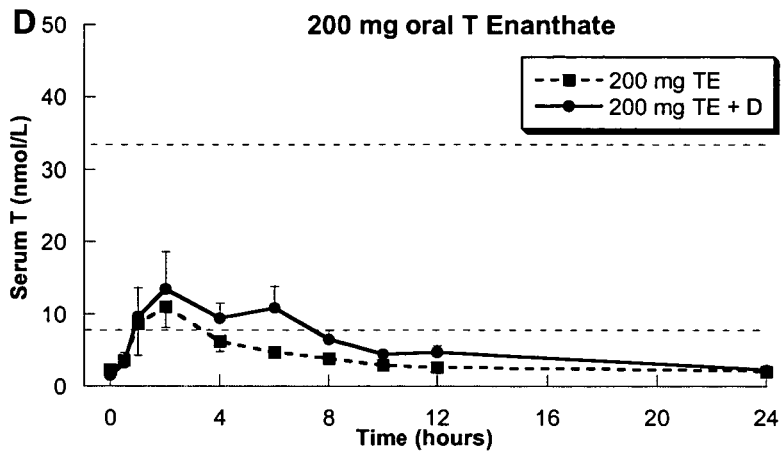
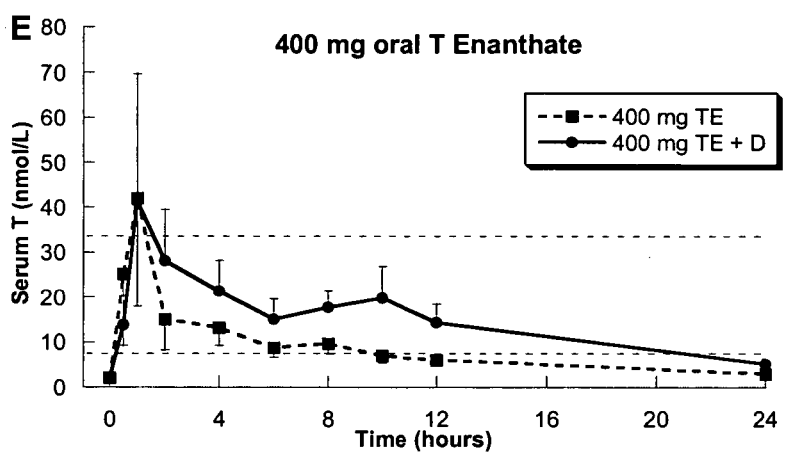
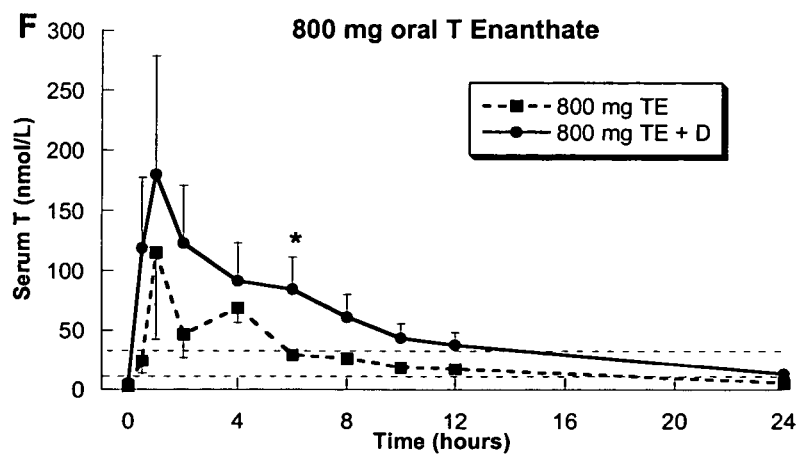
*Figure 7D-F*

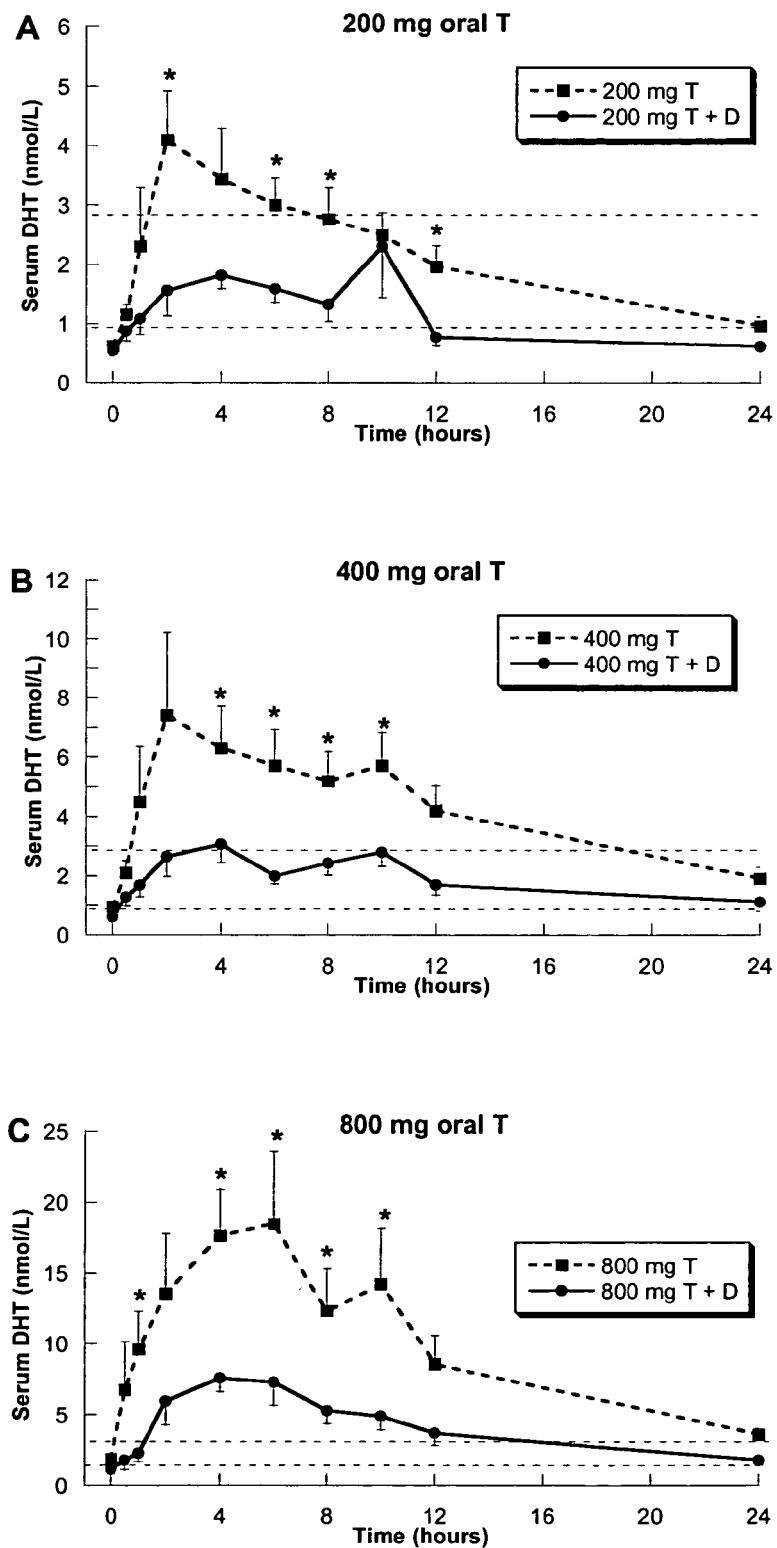
Figure 9A-C

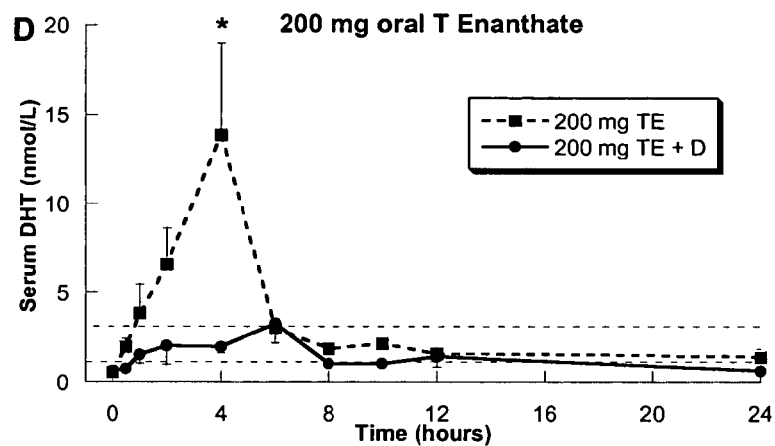
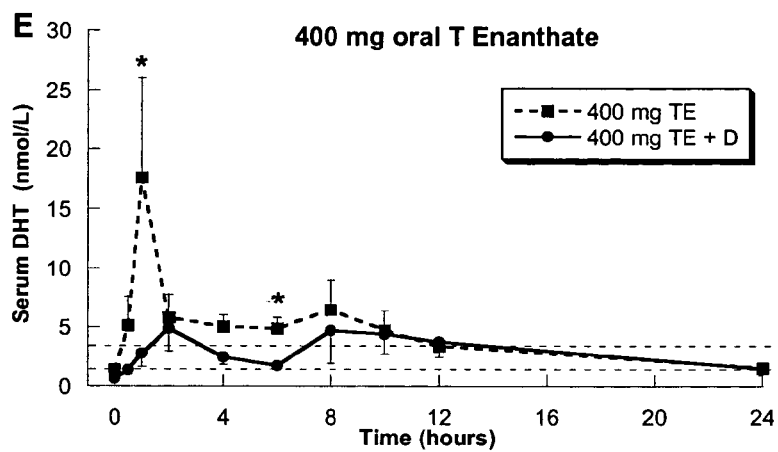
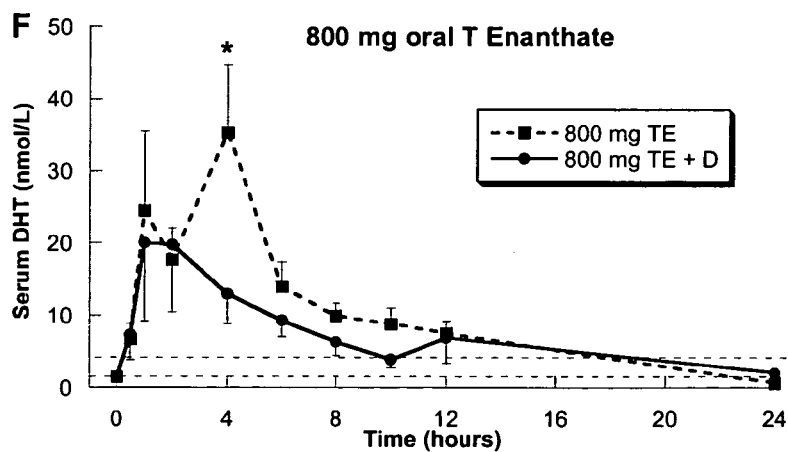
*Figure 9D-F*

ORAL ANDROGEN THERAPY USING MODULATORS OF TESTOSTERONE BIOAVAILABILITY

CROSS-REFERENCES TO RELATED APPLICATIONS

This application claims benefit of U.S. Provisional Patent Application No. 60/542,895 filed on Feb. 9, 2004 and incorporated by reference herein in its entirety.

STATEMENT AS TO RIGHTS TO INVENTIONS MADE UNDER FEDERALLY SPONSORED RESEARCH OR DEVELOPMENT

This work was supported by the National Institute of Child Health and Human Development, a division of the National Institute of Health, through grant #1K23 HD45386-10A1 and through cooperative agreements U54-HD-12629 and U54 HD42454 as part of the specialized Cooperative Centers Program in Reproductive Research and the Cooperative Contraceptive Research Centers Program. A portion of this work was conducted through the Clinical Research Center facility at the University of Washington and supported by the NIH grant M01-RR-00037. The United States Government and these Institutes may have certain rights in this application.

REFERENCE TO A "SEQUENCE LISTING," A TABLE, OR A COMPUTER PROGRAM LISTING APPENDIX SUBMITTED ON A COMPACT DISK.

NOT APPLICABLE

FIELD OF THE INVENTION

This invention relates to the use modulators which increase the bioavailability of testosterone, testosterone esters, and testosterone precursors orally administered in an oil vehicle. The modulators may be used in androgen therapy for both men and women and include dutasteride and finasteride. The androgen therapy can be directed, for instance, toward treatment of testosterone deficiency states, osteoporosis, muscle weakness, reduced libido, depression, hypogonadism, or male hormonal contraception.

BACKGROUND OF THE INVENTION

Testosterone is crucial for male health. The normal human male testes produces four to eight milligrams of testosterone daily. There is considerable variation in the reported half-life of testosterone, reported values range from 10 to 100 minutes. Circulating testosterone exhibits a diurnal variation in normal young men. See, Southren A K, et al., *J Clin Endocrinol* 27:686–694 (1967). Testosterone levels peak at about approximately 6:00 to 8:00 a.m. and decline during the remainder of the day. This testosterone has effects on a variety of tissues including, for instance, brain, liver, muscle, bone and bone marrow, blood vessels, skin, prostate and penis. Men with testosterone deficiency may have symptoms of depression, reduced libido, and low energy. They may suffer from anemia, osteoporosis and debilitating muscle weakness. Testosterone replacement therapy can improve well-being, maintain bone and muscle mass, and retain healthy sexual function.

Testosterone is also important in women's health. Androgens are secreted by both the ovaries and adrenal glands in women. Provision of testosterone in androgen-deficient women can improve their libido, energy, muscle mass and strength, and bone mineral density.

In the United States, testosterone replacement therapy primarily involves administration of testosterone by intramuscular injection, transdermal patch, or gels. The intramuscular injections must be given every 1–3 weeks to maintain normal serum testosterone levels and can be painful. Testosterone patches may cause moderate to severe skin reactions in more than half of subjects due to the vehicle that facilitates testosterone absorption across the skin. The testosterone gel is effective but expensive and care must be taken to avoid inadvertent exposure to women and children.

In the United States there are no FDA approved non-alkylated (and therefore safe) testosterone oral medications for administering testosterone. Thus, improved oral therapies for testosterone replacement are greatly needed. However, oral administration of unmodified testosterone at doses up to 100 mg have little effect on serum testosterone levels in levels deficient men (see, Foss G L, et al. *Lancet* 1:502–504(1939) and Nieschlag E, et al., *Acta Endocrinol (Copenh)* 79:366–374 (1975)). Several decades ago, 200 mg doses of oral testosterone were shown to elevate serum testosterone levels to the low normal range for up to eight hours (see, Johnsen S G et al., *Lancet* 2:1473–1475 (1974) and Daggett P R et al., *Hormone Res.* 9:121–12922,23 (1978)). Such serum testosterone levels were thought to be insufficient for clinical use and research into using unmodified oral testosterone was largely abandoned. A second issue relating to oral testosterone therapy is elevations in the potent androgen dihydrotestosterone (DHT) derived from conversion of testosterone by the enzyme 5-α reductase. Alkylated steroids having greatly improved oral bioavailablity have been developed. However, alkylation has been associated with a greatly increased risk of hepatotoxicity. Therefore, these synthetic compounds are far from an ideal solution.

Testosterone undecanoate (TU) is a testosterone ester currently used clinically in Europe and Canada for the treatment of testosterone deficiency. Oral TU therapy results in therapeutic increases in serum testosterone; however, it also results in elevations in serum DHT well above the normal range. Administration of lower doses of 100–200 mg doses of unmodified testosterone or non-alkylated "esterified" testosterone to testosterone deficient men does not elevate serum testosterone levels into the therapeutic range. A principal difficulty with the administration of oral testosterone is its rapid absorption into the hepatic circulation and subsequent destruction in the liver. The large doses that would be required to maintain therapeutic levels of testosterone over the course of therapy make testosterone therapy by oral administration impractical (Daggert et al. *Hormone Research* 9:121–129 (1978) and non-oral routes of administration of testosterone are much preferred. It is thought that specifically with testosterone undecanoate that some small portion of a large oral dose may be actually absorbed via the lymphatic system and thus avoid the 'first pass' effect of hepatic metabolism on the bioavailability of oral testosterone. Oral methods also may suffer from undesirable pharmacokinetic profile. They can result also in supra-physiologic testosterone concentrations followed by a too-rapid return to baseline.

A third issue relating to oral testosterone therapy is the role of food in the absorption of TU. The absorption of TU is dramatically improved by food intake due to the lipid-like structure of TU (see, Bagchus W M et al., *Pharmacotherapy* 23(3):319–25 (2003)). Knowledge of the affect of food on the absorption of orally dosed testosterone and testosterone esters will be very important in future studies of androgen therapy.

While overall only a very small fraction of endogenously produced testosterone is metabolised to DHT, a major factor in testosterone therapy is the conversion of testosterone to dihydrotestosterone (DHT). In some target organs, DHT is the more active androgen and the effects of testosterone are mediated by the conversion of testosterone to DHT by 5-α-reductase activity in the target organ. Both testosterone and DHT are metabolized to androstandiol, the 3α-diol of DHT that is rapidly metabolized by glucuronide conjugation and excreted in the urine. Observations of males with 5-α-reductase deficiency suggest that muscle, the penis, spermatogenesis, maintenance of libido, sexual behavior, and feedback inhibition of gonadotropin secretion primarily respond to testosterone whereas skin and the prostate primarily respond to DHT and that inhibitors of 5-α-reductase would be useful for the treatment or prevention of acne, baldness, female hirsutism, benign prostate hypertrophy, and prostatic cancer. Thus, the formation of DHT from testosterone and the effects of DHT on such target organs can be greatly reduced by adminstration of 5-α-reductase inhibitors.

Two isoenzymes of 5-α-reductase have been found: Type 1 and Type 2. The isoenzymes vary in their target tissue distribution (Rittmaster, *J. of Andrology* 18(6):582 (1997). 5α-reductase Type I is found largely in skin and the liver, while 5α-reductase Type II is located mainly in the male urogenital tract both during fetal and adult life. For instance, Type 1 predominates in the sebacious glands and Type 2 predominates in the prostate gland and hair follicles. Finasteride is predominantly an inhibitor for the Type 2 isoenzyme. Administration of finasteride has been reported to reduce serum DHT levels by 70% and prostate DHT levels by 90%. Combined inhibition of the Type 1 and Type 2 isoenzymes can reduce circulating DHT levels by 97%. While adminstration of finasteride can reduce serum DHT levels by 70%, the levels of testosterone itself are not appreciably changed. Typically testosterone levels only increase by about 10% in men given finasteride (Gormley et al. *J. Clin. Endocrinol. Metab.* 7:1136–41 (1990).

The combined use of exogenous androgen therapies with a 5-α-reductase inhibitor has been recently disclosed (see Amory et al., *J. Clin. Endocrinol. and Metabol.* 89(2): 503–510 (2004); see also U.S. Pat. No. 6,696,484 to Liao et al; U.S. Patent Application Publication No. 20030203043; and U.S. Patent Application Publication No. 20040110733). Amory et al., in particular, have investigated the effects of intramuscularly administered testosterone and the intramuscularly administered testosterone with finasteride in men with low serum testosterone. Amory et al. reported that finasteride greatly decreased serum DHT levels in the men but that finasteride was without substantial effect on the levels of serum testosterone in the men who received the testosterone by intramuscular administration.

The present invention provides for a practical means of oral androgen therapy. The invention is based upon the surprising discovery that despite the relatively minor role of 5-α-reductase to the overall metabolism or serum level of testosterone, orally administered finasteride and dutasteride nevertheless greatly increase the availability of testosterone and testosterone esters when these androgens are administered by the oral route as opposed to other routes (e.g., intramuscular, transdermal). With this discovery, it becomes practical to provide oral testosterone replacement therapy by administering testosterone, testosterone esters, and testosterone precursors in a combination therapy with modulators of testosterone bioavailability by the oral route.

BRIEF SUMMARY OF THE INVENTION

In several aspects, this invention provides methods and compositions for use in oral androgen therapy. In a first aspect, the invention provides methods of providing androgen therapy by orally administering to the subject an androgen which is in an oil vehicle and which is selected from the group consisting of testosterone, testosterone esters, and testosterone precursors and also by administering to the subject a modulator of testosterone bioavailability. In exemplary embodiments, the modulator is a compound having the formula:

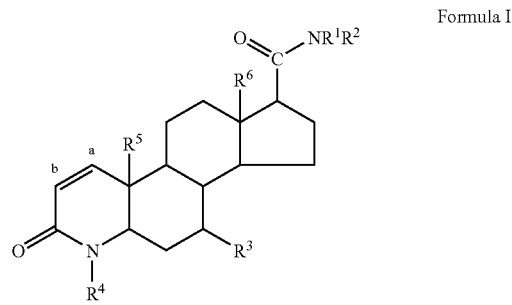

Formula I wherein $R^1$ is hydrogen or lower alkyl, and $R^2$ is optionally substituted alkyl or optionally substituted phenyl wherein the phenyl has 0, 1, 2, or 3 substituents selected from the group consisting of lower alkyl, halogen, and trifluoromethyl, and $R^3$, $R^4$, $R^5$, and $R^6$ are independently selected from the group consisting of hydrogen and optionally substituted lower alkyl, and the bond between adjacent carbon atom a and carbon atom b can optionally be replaced by a single bond with carbons a and b independently substituted with hydrogen or methyl, and the pharmaceutically acceptable salts thereof. The orally administered androgen is formulated in an oil vehicle. In some embodiments, the testosterone ester is testosterone propionate, testosterone enanthate, testosterone cypionate, testosterone triglyceride, or testosterone undecanoate. In some embodiments, the testosterone ester is not testosterone undecanoate. In other embodiments, the modulator is finasteride or dutasteride. In further embodiments, the androgen is testosterone or a testosterone ester and the modulator is finasteride or dutasteride. The androgen and modulator may be co-formulated or administered separately. The oil vehicle for the androgen can be any pharmaceutically acceptable oil. Suitable oils include, for instance, vegetable, fish, and mineral oils. In each of the above embodiments, the subject can be human.

The therapeutic regimen can be tailored by one of ordinary skill in the art to the condition to be treated. In some embodiments, therefore, the regimen may be acute, subchronic, or chronic. The duration of therapy may be open-ended or according to the duration of the condition to be treated or prevented.

In some embodiments, the androgen is administered to a human male subject in a daily dose of about or less than 400 mg/day, 300 mg/day. 200 mg/day, 100 mg/day or 50 mg/day. The dosage regimen may be daily, or the dosages may be subdivided for administration 2, 3 or 4 times per day.

In some embodiments, the androgen therapy is an androgen replacement therapy directed toward males. In androgen replacement therapy, the androgen therapy can be administered to a male having a serum testosterone level of less than 12 nmol/L or 6 nmol/L or 2 nmol/L. In other such embodiments, the men may also have one or more symptoms of depression, reduced libido, low energy and may suffer from any one of anemia, osteoporosis and muscle weakness. The androgen replacement therapy may be used to treat hypogonadism or orchiectomy or to provide male hormonal contraception.

In other embodiments, the androgen therapy is administered to improve mood or well-being, energy, maintain bone and muscle mass, and retain healthy sexual function or interest in men and women. In yet other embodiments, the androgen therapy may be administered to male or female burn, trauma, chronic illness, or perioperative patients to promote healing or body composition of fat, bone, protein, or muscle. The therapy may be directed toward increasing testosterone levels which decrease with age or to increase a low sex drive in humans. The therapy may be directed toward reducing the wasting associated with being HIV+ or being elderly (e.g., age-related sacropenia). In additional embodiments, the androgen therapy is used in male contraception, particularly humans.

In another aspect the invention is drawn to a method of increasing the oral availability of orally administered testosterone and testosterone esters in oil by also administering a modulator of testosterone bioavailability. The modulator can be a modulator of Formula I, including but not limited to, finasteride and dutasteride. In some embodiments, administration of the modulator increases the bioavailability of the orally administered testosterone or testosterone ester is increased by at least about 30%, 50% or 75%.

In another aspect the invention is drawn to an oral pharmaceutical composition comprising a modulator of testosterone bioavailability and an androgen which is testosterone, a testosterone ester, or a testosterone precursor in a suitable oil vehicle. In some embodiments, the modulator is finasteride or dutasteride. In other embodiments, the androgen is in a unit dosage format comprising less than about 500 mg, 400 mg, 300 mg, 200 mg, 100 mg, 50 mg, or 25 mg of the androgen. In a further embodiment, the androgen is in a unit dosage format comprising less than about 500 mg, 400 mg, 300 mg, 200 mg, 100 mg, 50 mg or 25 mg of the androgen and the modulator is dutasteride or finasteride. In a further embodiment thereof, the androgen is in a unit dosage format comprising less than about 500 mg, 400 mg, 300 mg, 200 mg, 100 mg, 50 mg or 25 mg of the androgen and the finasteride or dutasteride is in an effective amount to modulate the bioavailability of the testosterone. In some embodiments, the oil vehicle is a fish oil, vegetable oil, or mineral oil.

In each of the above aspects, the modulator need not be an 5-α-reductase inhibitor. Thus, in some embodiments the modulator of formula I is not appreciably an inhibitor of either or both Type 1 and Type 2 isoenzymes of 5-α reductase. In some embodiments, the modulator can be inhibitor of either or both Type 1 and Type 2 isoenzymes of 5-α reductase.

In each of the above aspects, in some embodiments the androgen is a testosterone precursor which is 4-androstenediol or 4-androstenedione.

In some aspects, the invention provides a means of identifying modulators of testosterone bioavailability by screening 5-α-reductase inhibitors or compounds of formula I for their ability to increase the bioavailability of testosterone, testosterone, esters or testosterone precursors when the subject androgen is administered orally in a oil vehicle and the modulator by comparing serum total testosterone levels or serum bioavailable testosterone levels in subjects administered the androgen without administration of the test modulator to subjects administered the androgen with administration of the test modulator. A agent is identified as a modulator if it increases the bioavailability of the administered androgen by at least 30%. In some embodiments, a more stringent cut off of 50% may be used. Bioavailability may be assessed as described further below.

In another aspect the invention provides a method of modulating the bioavailability of testosterone, a testosterone ester, or a testosterone precursor orally administered in an oil vehicle to a subject by also administering to the subject a modulator of testosterone bioavailability. In one embodiment, the modulator is a compound of Formula I. In another embodiment, the compound is a 5-α-reductase inhibitor. In another embodiment, the modulator is dutasteride or finasteride. The modulator may be administered before or concurrently with the testosterone, testosterone ester or testosterone precursor.

In each of the above aspects, in some embodiments, the subject receiving the androgen therapy, androgen, or pharmaceutical composition can be a human or another mammal (e.g., rabbit, rodent, dog, cat) or farm animals (e.g., cow, sheep, pig, horse, goat, bull, fowl). The subject (e.g., a human subject) may be fasting or fed at the time of the androgen administration.

BRIEF DESCRIPTION OF THE DRAWINGS

FIG. 1. Study Design. Following the control period, 8 male subjects underwent the following treatment: (Day 0) Acyline 300 µg/kg once, followed 24 hours later (Day 1) by testosterone 400 mg po once, with breakfast, followed 24 hours later (day 2) by finasteride 5 mg po bid, followed 24 hours later (day 3) by finasteride 5 mg and 30 minutes later testosterone 400 mg po once, given while fasting, followed 24 hours later (Day 4) by finasteride 5 mg po once, then 30 minutes later testosterone 400 mg po once with food. Subjects came in on day 5 for a brief blood draw. There was no drug administration on days 5 or 6. On day 7, subjects took dutasteride 0.5 mg po bid, then on day 8 then retook dutasteride 0.5 mg once, then 30 minutes later receive testosterone 400 mg po once while fasting, followed 24 hours later (Day 9) by dutasteride 0.5 mg po once, followed 24 hours later (day 10) by dutasteride 0.5 mg po once followed 30 minutes later by testosterone 400 mg po once, given with breakfast, on day 11 subjects came in for an early morning blood draw only.

FIG. 7. Serum Testosterone after oral administration of 200, 400 and 800 mg of testosterone in oil (A–C) and testosterone enanthate in oil (D–F) with and without dutasteride for 24 hours in normal men treated with the GnRH antagonist acyline to temporarily suspend testosterone production. The dotted lines represent the upper and lower limits of the normal range for serum testosterone. $P<0.05$ compared with testosterone alone.

FIG. 9. Serum Dihydrotestosterone (DHT) after oral administration of 200, 400 and 800 mg of testosterone in oil (A–C) and testosterone enanthate in oil (D–F) with and without dutasteride for 24 hours in normal men treated with the GnRH antagonist acyline to temporarily suspend testosterone production. The dotted lines represent the upper and lower limits of the normal range for serum DHT. *$P<0.05$ compared with testosterone with dutasteride FIG. 10. Serum and sex-hormone binding globulin levels after oral administration of 200, 400 and 800 mg of testosterone and testosterone enanthate in oil with and without dutasteride for 24 hours in normal men treated with the GnRH antagonist acyline to temporarily suspend testosterone production. The dotted lines represent the upper and lower limits of the normal range *$P<0.05$ compared with baseline

DETAILED DESCRIPTION

Figure 2A:
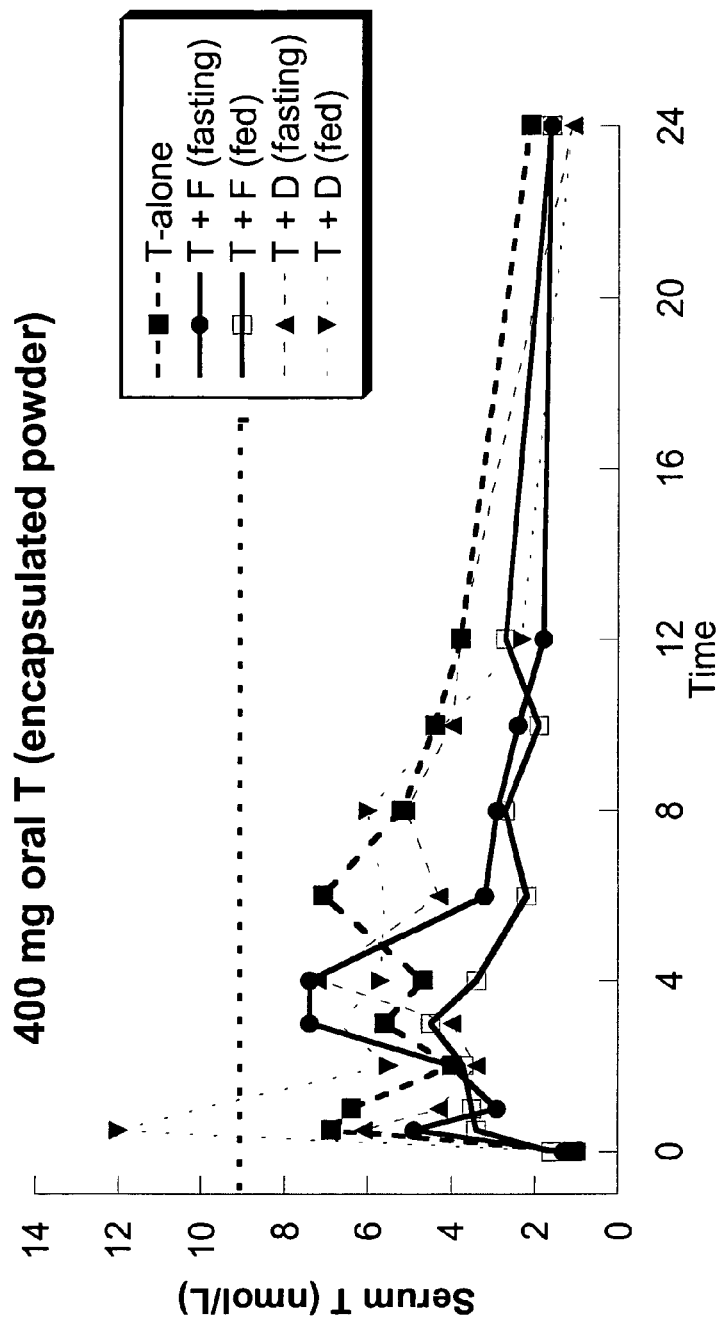
FIG. 2. Effect of dutasteride and finasteride administration on mean total serum testosterone levels (FIG. 2A) and DHT levels (FIG. 2B) in men orally administered testosterone per the protocol of FIG. 1. Encapsulation of the oral testosterone powder (i.e. not the oil) was performed in the University of Washington compounding pharmacy. The pharmacist packed 400 mg po micronized testosterone into a #18 blue capsule. The symbols represent statistical significance of a) T+D (stars) and b) T+F (psi) compared with placebo at P<0.05. There were no significant differences between T+F vs. T+D. in encapsulated form.

The Applicants herein report an unexpected synergism of the compounds of Formula I and testosterone, testosterone esters and testosterone precursors when the testosterone, testosterone esters or testosterone precursor is administered by the oral route and is formulated in an oil vehicle. The combined therapy of a compound of Formula I with oral administration of testosterone (FIGS. 3, 7) or a testosterone ester (FIG. 7) formulated in oil is shown to greatly increase the bioavailability of the orally administered testosterone ester in fed or fasting men. This unexpected and surprising finding stands in sharp contrast to the results to be obtained by the oral administration of the combination of oral doses of testosterone, testosterone ester, or testosterone precursor when orally administered in encapsulated powder. In the case of the testosterone ester administered as an encapsulated powder to fed or fasting men, compounds of Formula I such as finasteride and dutasteride are without much effect on the bioavailability of the orally administered testosterone (see FIG. 2). Consistent with much of the prior literature concerning the relatively minor effect of 5-α reductases in the overall metabolism or serum levels of endogenously produced testosterone, the Applicants have also found that adminstration of the compounds of Formula I do not have much effect on testosterone levels themselves in men administered testosterone intramuscularly. See, Amory et al., J. Clin. Endocrinol. Metabol. 89(2):503–510 (2004) which is incorporated herein by reference in its entirety and also particularly with respect to the disclosures of the methods and subject matter pertaining to FIG. 1 thereof which show that finasteride has very little effect on serum testosterone while greatly inhibiting serum DHT levels in men given testosterone enanthate by intramuscular injection.

The invention can thus provide an improved and practical approach to testosterone therapy which can be more convenient, safe, effective, and selective. The convenience lies in the oral administration which is generally less troublesome than other routes of administration. The safety lies in the absence or reduction in the supraphysiologically harmful elevation in serum levels of DHT. The efficacy relates to the therapeutic serum levels of testosterone that can be readily achieved and maintained. The selectivity in part relates to the choice of the compound of Formula I (e.g., selection of a Type I, Ttype II, or nonselective inhibitor of 5-α reductase). The choice affects the conversion of testosterone to DHT according to the type of the isoenzyme in the target tissue.

The mechanism(s) by which this suprising effect of the compounds of formula I is(are) achieved is uncertain. As hepatic metabolism is thought to be the principle barrier to the absorption of testosterone from the GI tract, it is likely that the effects of these modulatory agents are mostly mediated by inhibition of the hepatic metabolism of testosterone, but not necessarily inhibition of the 5-α-reductase activity, but possibly via inhibition of androgen metabolism by cytochrome P450(CYP3A4). While it has been shown that the 5a reductase activity in the liver is mainly type 1, both finasteride (a type II inhibitor) and dutasteride are each very effective in modulating the bioavailability when the testosterone is administered in oil. It is also not clear why the bioavailability of testosterone upon oral administration of the testosterone in oil is greatly benefited by co-administration of either finasteride or dutasteride but administation of testosterone encapsulated as a powder is not. In this regard, it should be noted that finasteride and dutasteride appear to have similar effects on testosterone bioavailability while the dual Type I and Type II 5-α-reductase inhibitor dutasteride is more effective in lowering serum DHT levels than the Type II selective inhibitor finasteride.

Whatever the mechanism of action, both finasteride and dutasteride are testosterone-like in structure and are compounds of the following general formula:

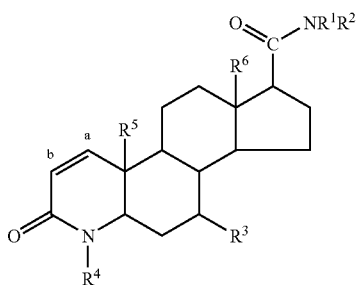

Formula I wherein $R^1$ is hydrogen or lower alkyl, and $R^2$ is optionally substituted alkyl or optionally substituted phenyl wherein the phenyl has 0, 1, 2, or 3 substituents selected from the group consisting of lower alkyl, halogen, and trifluoromethyl, and $R^3$, $R^4$, $R^5$, and $R^6$ are independently selected from the group consisting of hydrogen and optionally substituted lower alkyl, and the bond between adjacent carbon atom a and carbon atom b can optionally be replaced by a single bond in which the adjacent carbons are independently substituted with hydrogen or methyl, and the pharmaceutically acceptable salts thereof.

Thus, without being wed to theory, in one aspect, the invention provides pharmaceutical compositions and methods for androgen therapy drawn in part to co-administration of the compounds of formula I with oral administration of testosterone, testosterone esters, and testosterone precursors in oil. Given the difficulties of dermal and subcutaneous and submuscular administration of androgens the present invention provides a great improvement in androgen therapy. Furthermore, insofar as DHT is the principal androgen involved in the pathogenesis of prostate disease, acne and male-pattern baldness, androgen therapy which selectively raises testosterone without increasing DHT can be a great improvement over existing forms of androgen therapy. Thus, there is an advantage to the embodiments wherein the modulator is also a 5-α-reductase inhibitor (e.g., Type I or Type II or nonselective inhibitor).

The invention therefore provides an effective and selective form of oral androgen therapy using testosterone, testosterone esters, or testosterone precursors and a modulator of testosterone bioavailability. The oral administration of testosterone, testosterone esters, or a testosterone precursor and a modulator of testosterone bioavailability in conjuction with administration of a modulator of testosterone bioavailability increases serum testosterone levels into the therapeutic range-something which would otherwise require much higher doses of oral testosterone without the concomitant administration of the modulator. In addition, the combination of oral testosterone and a modulator of testosterone bioavailability provides selectivity in androgen therapy, increasing serum testosterone (beneficial to muscle, bone, sexual health and well-being) without increasing serum dihydrotestosterone (which causes prostate enlargement, acne and male pattern baldness). Moreover, the oral route is more convenient than the currently existing options for androgen therapy, namely: injections, pellets, patches and gels.

This improved and easily administered form of androgen therapy can be used in humans for the treatment of testosterone deficiency in men, for the relative androgen deficiency states of aging, for male hormonal contraceptives, recovery from surgery, recovery from burns and, due to its selectivity, be useful for the above indications for androgen therapy for women. This form of androgen therapy is also useful in any situation where increasing testosterone levels without also raising dihydrotestosterone levels is beneficial, including but not limited to increasing growth and muscle mass of farm animals such as cattle.

DEFINITIONS

It is noted here that as used in this specification and the appended claims, the singular forms "a," "an," and "the" include plural reference unless the context clearly dictates otherwise.

Unless defined otherwise, all technical and scientific terms used herein have the meaning commonly understood by a person skilled in the art to which this invention belongs. The following references provide one of skill with a general definition of many of the terms used in this invention: Singleton et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); THE GLOSSARY OF GENETICS, 5TH ED., R. Rieger et al. (eds.), Springer Verlag (1991); and Hale & Marham, THE HARPER COLLINS DICTIONARY OF BIOLOGY (1991). As used herein, the following terms have the meanings ascribed to them unless specified otherwise.

For the purposes herein androgen therapy seeks to increase androgen activity and levels in male or female subjects by administering testosterone, testosterone esters, or a testosterone precursor to a subject. Subjects in need of androgen therapy are well known to one of ordinary skill in the medical and veterinary arts. For instance, the androgen therapy can be given to patients with muscle weakness or reduced muscle mass to increased muscle mass and strength, to patients with osteoporosis to increase mineral bone density and bone strength, with patients having a reduced libido to increase sexual interest and activity or performance, to patients with low energy to increase energy levels, or patients with low hematocrits to increase the hematocrit. The therapy may be administered to depressed patients to improve mood and alleviate depression. Androgen therapy can be generally directed toward increasing (or preventing loss of) muscle mass or strength, increasing (or preventing loss of) bone density; or increasing (or preventing reductions in) hematocrit. Androgens therapy can be used to stimulate red blood cell production by enhancing production of erythropoietic stimulating factors. Androgen therapy can be used to increase protein anabolism. Androgen therapy can be used to treat burn or perioperative patients to promote healing and/or maintenance of muscle mass. The androgen therapy may be administered to men for purposes of contraception. The androgen therapy may be used to treat AIDS associated wasting in HIV+ males and females and, particularly, men and women.

With respect to women, diagnosis of a testosterone deficiency is known to the average physician practicing in the relevant field of medicine. For instance, androgen therapy can be directed to women for whom androgen production is deficient due to treatment with oral contraceptives, adrenal dysfunction, removal of one or both ovaries, hysterectomy, post-menopausal estrogen replacement therapy, corticosteroid treatment-induced adrenal suppression, and human immunodeficiency virus-positive status, panhypopituitarism; and chronic illness, such as systemic lupus erythematosis, rheumatoid arthritis, chronic obstructive lung disease, and end stage renal disease. Major objectives and physiological benefits of androgen therapy in women include, but are not limited to anabolic effects on muscle, skin, hair and bone; stimulatory effects on erythropoiesis; modulatory effects on immune function; and psychological effects on mood, well-being and sexual function. Androgen deficiency in women can be specifically diagnosed also by monitoring serum testosterone levels.

As used herein, the phrases "androgen deficiency" or "testosterone deficiency" are used interchangeably, and refer to lower serum levels of bioavailable testosterone or total serum testosterone in a subject as compared to the median serum bioavailable levels or total serum testosterone levels for healthy subjects of the same age and gender. In adult human males, a serum total testosterone level of 12 nmol/ml or less is generally indicative of androgen deficiency. The level is preferably measured in the early morning when testosterone levels peaks during the normal circadian rhythm.

Androgen replacement therapy is a form of androgen therapy which seeks to increase testosterone activity and levels in males or females with deficient serum testosterone levels by administering testosterone, testosterone esters or testosterone precursors. In pubertal and adult human males, testosterone is the major circulating androgen in blood and androgen replacement therapy can be directed toward the adult or pubertal males of any age having a total serum testosterone level of less than 14 nmol/L, 12 nmol/L, 10 nmol/L, 8 nmol/L, 6 nmol/L, 4 nmol/L or 1 nmol/L. levels. Such individuals may be hypogonadal males or males having had orchectomy or aging males whose testosterone levels have declined with time. The therapy may be administered to treat congenital, age-related, or any acquired deficiency of endogenous testosterone.

With respect to women, injection of testosterone is also approved for the treatment of metastatic breast cancer. Androgen replacement therapy may also be directed toward women having total serum testosterone levels of about or less than 0.5 nmol/L. Such therapies may be directed toward any one or more of increasing the serum testosterone level, improving mood, energy, libido, alleviating depression, increasing (or preventing loss of) muscle mass or strength, increasing (or preventing loss of) bone density; increasing (or preventing reductions in) hematocrit in the treated subject.

Of particular note, without limitation thereto, androgen therapy may be directed in men or women for the restoration, enhancement, or improvement of sexual desire, frequency of sexual activity, stimulation to sexual organs, ability to achieve orgasm, pleasure in sexual activity, vital energy, sense of well-being, mood and sense of emotional well being, shyness, cognitive abilities, muscle mass and function, body composition (e.g., reduced body fat), hematocrit, bone mineral density, skin and hair condition, pubic hair. In women, androgen therapy may also be used to treat urogenital atrophy, vaginal dryness, dry eyes, autoimmune conditions, vasomotor instability, breast tenderness, symptoms of premenstrual syndrome, and a combination thereof.

Bioavailable testosterone accounts for about half the total amount of testosterone in serum. About 98% of blood testosterone is bound to serum proteins. Approximately 40% of circulating plasma testosterone binds to sex hormone-binding globulin (SHBG), 2% remains unbound (free), and the remainder binds to albumin and other proteins. Testosterone binds with high affinity to the sex-steroid binding globulin and binds with low affinity to albumin. The fraction bound to albumin dissociates easily and is presumed to be biologically active, whereas the SHBG fraction is not. The term "free" testosterone as used herein refers to the fraction of testosterone in the blood that is not bound to protein. The term "total testosterone" or "testosterone" as used herein means the free testosterone plus protein-bound testosterone. The term "bioavailable testosterone" as used herein refers to the non-sex hormone binding globulin bound testosterone and includes both that weakly bound to albumin and the free form of testosterone.

Testosterone has a hydroxy group at the 17 position. This hydroxy group can be esterified. Testosterone esters have an ester group, for example, propionate ($OOCCH_2CH_3$) at the 17 position of testosterone. Exemplary esters include testosterone proprionate, testosterone enanthate, testosterone cypionate, testosterone undecanoate, cyclohexylmethylcarbonate, and testosterone triglyceride. Additional testosterone esters can include, and are not limited to, the formate, acetate, butyrate, valerate, hexanoate, heptanoate, octanoate, nonanoate, decanoate. A longer ester hydrocarbon chain can provide a more favorable water/oil partition coefficient. Typically, esterase activities in vivo can readily hydrolyze the ester linkage to release the testosterone moiety. In some embodiments, the testosterone ester is either the undecanoate or the triglyceride ester. In other embodiments, the testosterone ester is neither the undecanoate or the triglyceride ester.

A testosterone precursor is a compound capable of being metabolized or converted in vivo to form testosterone. Exemplary precursors of testosterone are androstenediol and 4-androstenedione. In some embodiments, the androgenic testosterone precursor can be selected from the group consisting of $\Delta^4$-androstene-3,17-dione, pregnenolone, dehydroepiandrosterone, $\Delta^4$-androstene-3β,17β-diol, $\Delta^5$-androstene-3β,17β-iol, 19-norandrost-4-ene-3,17-dione, 19-norandrost-4-ene-3β,17β-diol, 19-norandrost-5-ene-3β,17β-diol.

Bioavailability is defined as the dose delivered to the serum divided by the dose administered. In general a modulator of testosterone bioavailability can increase bioavailability of testosterone by at least 30%, 50% or 70%. A modulator of testosterone bioavailability is a compound which increases by at least 30% the bioavailability of testosterone, testosterone esters, or a testosterone precursor orally administered in an oil vehicle to adult human males or females. The modulatory activity is preferably ascertained by monitoring total serum testosterone levels for each subject over a define period (e.g., 2, 4, 6, 8, 12, or 24 hour period) following the administration of an oral dose of a testosterone ester (e.g., testosterone enanthate). The modulation is with respect to the orally provided testosterone and not the endogenously produced testosterone. The percent increase can be based upon comparisons of the area under the resulting serum testosterone level vs. time curve for a test group administered testosterone enanthate and the candidate modulator and a test group administered testosterone enanthate and a placebo in place of the modulator.

In some embodiments, the modulator is capable of increasing testosterone bioavailability by at least 50% or 75%.

In yet additional embodiments, the modulators of the present invention are preferably compounds of Formula I:

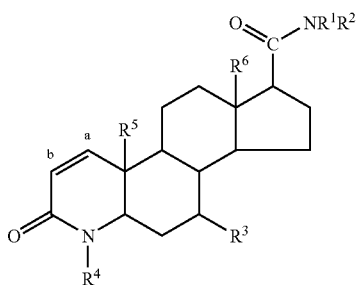

Formula I wherein R¹ is hydrogen or lower alkyl, and R² is optionally substituted alkyl or optionally substituted phenyl wherein the phenyl has 0, 1, 2, or 3 substituents selected from the group consisting of lower alkyl, halogen, and trifluoromethyl, and R³, R⁴, R⁵, and R⁶ are independently selected from the group consisting of hydrogen and optionally substituted lower alkyl, and the bond between adjacent carbon atom a and carbon atom can optionally be replaced by a single bond in which the adjacent carbons are independently substituted with hydrogen or methyl, and the pharmaceutically acceptable salts thereof. In some embodiments, the bond between carbon a and carbon b is a double bond and R² is unsubstituted lower alkyl or unsubstituted phenyl. In additional embodiments, the bond between carbon a and carbon b is a double bond and R³, R⁴, R⁵, and R⁶ are each independently selected from hydrogen or unsubstituted $C_1-C_4$ alkyl. In some embodiments, the bond between carbon a and carbon b is a double bond and R³, R⁴, R⁵, and R⁶ are independently selected from hydrogen, methyl, and ethyl. In still other embodiments, the bond between carbon a and carbon b is a double bond, R¹ is hydrogen, R² is substituted phenyl and R³, R⁴, R⁵, and R⁶ are independently selected from hydrogen and methyl. In yet other embodiments, the bond between carbon a and carbon b is a double bond, R¹ is hydrogen, R² is unsubstituted lower alkyl and R³, R⁴, R⁵, and R⁶ are independently selected from hydrogen and methyl. In some embodiments, the bond between carbon a and carbon b is a double bond, R¹ is hydrogen, R² is unsubstituted lower alkyl, R³ and R⁴ are each hydrogen, and R⁴ and R⁵ are each methyl. In some embodiments, the compound is finasteride or dutasteride. In still other embodiments the bond between adjacent carbons a and b is a replaced by a single bond in which the adjacent carbons are independently substituted with hydrogen or methyl. In each of the above embodiments, there is a further embodiment wherein the alkyl or lower alkyl subject matter is limited to saturated alkyl or lower alkyl groups or saturated and unsubstituted alkyl or lower alkyl groups.

Additional modulators are 4-aza-17β-substituted -5α-androstan-3-one compounds taught in U.S. Pat. No. 4,377,584 which is incorporated herein by reference in its entirety and incorporated with particularity also with respect to the compounds disclosed therein and the methods of making them. In some embodiments, the modulator is also a 5-α-reductase inhibitor which may be non-selective or selective for the type 1 or type 2 isoenzyme.

Additional modulators having a testosterone-like molecular structure and suitable for use in the oral androgen therapy of the present invention are 17β-anilide-4-aza-5α-androstan-3-ones taught in U.S. Pat. No. 5,998,427 which is incorporated herein by reference in its entirety and with particularity in respect to the compounds disclosed therein.

In some embodiments, the modulators are also 5-α-reductase inhibitors which may be non-selective or selective for the type 1 or type 2 isoenzyme.

In one embodiment, the modulator for use in the androgen therapy of the present invention is SKF105657:

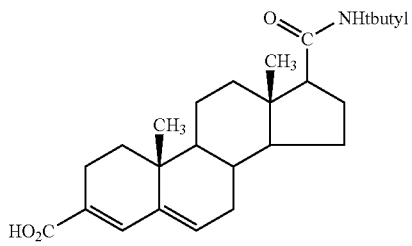

In one embodiment, the modulator for use in the androgen therapy is finasteride:

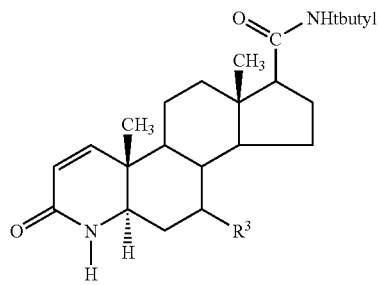

Modulating testosterone bioavailability refers to increasing the testosterone bioavailability of testosterone, testosterone esters, or testosterone precursors, when such is administered in an oil vehicle or carrier, by at least 30%, and more preferably by at least 50%, or 75% by also administering a modulator of testosterone bioavailability.

Compounds for use according to the invention may contain one or more asymmetric centers and can thus occur as racemates and racemic mixtures, single enantiomers, diastereomeric mixtures and individual diastereomers. The present invention is meant to comprehend all such isomeric forms of the inventive compounds.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed by the inventive formulas.

Alternatively, any enantiomer of a compound for use in the present invention may be obtained by stereospecific synthesis using optically pure starting materials or reagents of known configuration.

The compounds for use in the present invention may have unnatural ratios of atomic isotopes at one or more of their atoms. For example, the compounds may be radiolabeled with isotopes, such as tritium or carbon-14. All isotopic variations of the compounds for use in the present invention, whether radioactive or not, are within the scope of the present invention.

Many organic compounds can form complexes with solvents in which they are reacted or from which they are precipitated or crystallized. These complexes are known as "solvates". For example, a complex with water is known as a "hydrate". Solvates of any of the modulatory compounds for use according to the invention are within the scope of the invention. It will also be appreciated by those skilled in organic chemistry that many organic compounds can exist in more than one crystalline form. For example, crystalline form may vary from solvate to solvate. Thus, all crystalline forms of the modulatory compounds for use according to the invention or the pharmaceutically acceptable solvates thereof are within the scope of the present invention.

The term "alkyl," by itself or as part of another substituent, means, unless otherwise stated, a straight or branched chain, or cyclic hydrocarbon radical, or combination thereof, which may be fully saturated, mono- or polyunsaturated, having the number of carbon atoms designated (i.e. $C_1$–$C_{10}$ means one to ten carbons). Examples of saturated hydrocarbon radicals include, but are not limited to, groups such as methyl, ethyl, n-propyl, isopropyl, n-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Examples of cycloalkyl include, but are not limited to, cyclopentyl, cyclohexyl, 1-cyclohexenyl, 3-cyclohexenyl, cycloheptyl, and the like. Alkyl groups may be substituted or unsubstituted. Lower alkyl refers to a $C_1$ to $C_6$ alkyl.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo ($C_1$–$C_4$)alkyl" is mean to include, but not be limited to, trifluoromethyl, 2,2,2-trifluoroethyl, 4-chlorobutyl, 3-bromopropyl, and the like. In some embodiments, the halogen substitutents are chloro. In other embodiments, the halogen substituents are fluoro.

Substituents for the lower alkyl, alkyl, and phenyl groups or radicals can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(R'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, unsubstituted alkyl or alkoxy. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" and "phenyl" is meant to include groups including carbon atoms bound to groups other than hydrogen groups, such as halophenyl, haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

The compounds for use in the present invention may be isolated and/or used in the form of their pharmaceutically acceptable acid addition salts, such as the salts derived from using inorganic and organic acids. The pharmaceutically or physiologically acceptable salts include, but not limited to, a metal salts such as sodium salt, potassium salt, lithium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, sulfate, phosphate and the like; organic acid salts such as formate, acetate, trifluoroacetate, maleate, tartrate and the like; and sulfonates; and amino acid salts such as arginate, asparginate, glutamate and the like.

Finasteride is also known as (5α,17beta)-N-(1,1-dimethylethyl)-3-oxo-4-azaandrost-1-ene-17-carboxamide and is clinically available as Propecia® and Proscar®.

Dutasteride is also known as (5',17β)-N-[2,5-Bis(trifluoromethyl)phenyl]-3-oxo-4-azaandrost-1-ene-17-carboxamide and is available as Avodart®.

The term "pharmaceutical composition" is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. The term "pharmaceutical composition" indicates a composition suitable for pharmaceutical use in a subject, including an animal or human. A pharmaceutical composition generally comprises an effective amount of one or more active agents (e.g., testosterone, testosterone ester, testosterone precurors, and/or a modulator of the bioavailability of such) and a pharmaceutically acceptable carrier.

The term "pharmaceutically acceptable carrier" encompasses any of the standard pharmaceutical carriers, buffers and excipients, including phosphate-buffered saline solution, water, and emulsions (such as an oil/water or water/oil emulsion), and various types of wetting agents and/or adjuvants. Suitable pharmaceutical carriers and their formulations are described in REMINGTON'S PHARMACEUTICAL SCIENCES (Mack Publishing Co., Easton, 19th ed. 1995). Suitable pharmaceutical carriers depend upon the intended mode of administration and the active agent. Typical modes of administration for modulators are described below.

The oil vehicle in which a testosterone, testosterone ester, or testosterone precursor can be orally administered may be, or principally composed of, a vegetable oil, fish oil, a mineral oil, or an oil approved for human consumption by the FDA. For example, the vegetable oil can be sesame oil, corn oil, peanut oil, olive oil, palm oil, coconut oil, cotton seed oil, flax seed oil, safflower oil, or sunflower oil, walnut oil, including mixtures thereof. For example, the fish oil can be salmon oil, tuna oil, sardine oil, cod liver oil, shark liver oil and mixtures thereof. When the modulator and testosterone, testosterone ester or testosterone precursor are co-formulated for oral administration they are preferably co-formulated in oil. Excipients including, for instance, antioxidants and stabilizers or solubilizers may be added. Flavorants or colorants may be added.

In some embodiments, the testosterone, testosterone ester, or testosterone precursor may be administered in an oil-like vehicle which may be or comprise one or more of a pharmaceutically compatible, and preferably digestable, lipid substance having as its primary constituent, for instance, (1) mono-, di- and triglycerides of fatty acids; (2) fatty acid esters or alcohols, higher aliphatic alcohols; (3) saturated or unsaturated fatty acids, higher aliphatic alcohols; (4) the mono-, di and triglyceride oils and glycerol ethers; and (5) certain types of wax. The oil-like vehicle may be liquid or semi-liquid. The lipid substance may preferably be liquid at ambient temperature, that is, at a temperature in the range of about 10° C. to about 30° C. The lipid substance or oil optionally may contain additional excipients, including hydrophobic or hydrophilic surfactants.

The term "effective amount" means a dosage sufficient to produce a desired result on health and/or on the bioavailability of orally administered testosterone. The desired result may comprise a subjective or objective improvement in the recipient of the dosage. A subjective improvement may be, for instance, improved mood, increased energy or strength, or libido. An objective improvement may be, for instance, increased muscle mass, bone density, hematocrit, or serum testosterone levels. or a decreased likelihood of developing a disease or harmful health condition.

Methods of Making Modulators of Formula I.

Methods of making the compound of formula I are well known in the art and taught in U.S. Pat. No. 4,377,684 which is incorporated by reference for all purposes.

Methods of Identifying Modulators of the Bioavailability of Orally Administered Testosterone, Testosterone Esters, or Testosterone Precursors.

Several of the examples below exemplify methods of screening compounds of Formula I for their modulatory activity with respect to the bioavailability of testosterone.

In general, screening can be performed in a mammal, preferably a human or a non-human male primate or the mammalian species and gender of particular interest. It may be advantageous to first screen compounds for modulatory activity in a non-primate model (e.g., rabbit, mouse, rat, and pig) before proceeding to screening in the human or non-human primate. Because testosterone synthesis and levels are subject to biofeedback inhibition and to avoid the difficulty in distinguishing endogenous from exogenously provided testosterone, it is advantageous to first inhibit testosterone production by administering an agent with gonadotropin-releasing hormone (GnRH) antagonist activity (e.g., acyline) to temporarily suspend endogenous testosterone production. Subsequent to the administration of the antagonist, the endogenous or background levels of testosterone will fall to inconsequential levels such that serum testosterone measurements will reflect the testosterone bioavailability of exogenously provided testosterone, testosterone esters, and testosterone precursors.

The GnRH subjects can be further divided into at least two groups. One group will be a placebo or vehicle group and the other group will be one or more experimental or modulator group. Additional modulator test groups can be used to explore dose response. The modulators may be administered concomitantly or shortly prior or, preferably, for a day or more prior to administration of the testosterone, testosterone ester, or testosterone precursor in oil. The modulators may be orally administered separately from, or co-administered with, the testosterone, testosterone ester, or testosterone precursor in oil. Once the background levels of endogenously produced testosterone have fallen to a level too low to confound the measurements of the exogenously provided, the subjects are orally administered testosterone, testosterone ester (e.g., testosterone enanthate), or testosterone precursor in oil and the serum bioavailable or total testosterone levels are monitored for a fixed period of time (e.g., 2, 4, 8, or 12 hours). Modulators are identified according to their ability to increase the serum bioavailable and/or total serum testosterone levels over the monitored period. This increase may be measured according to the area under the serum bioavailable testosterone level- or serum total testosterone level-time curve for a given or predetermined period (e.g., 2, 4, 8, or 12 hours). This increase may also be determined or statistically assessed by comparing the average levels obtained for the modulator group and its control group at a single time point (e.g., 2, 4, 8, or 12 hours).

Additionally, it may be possible to prescreen compounds for their modulatory activity be testing candidate modulators for their ability to inhibit the metabolism of testosterone in vitro. This alternative means can be accomplished by contacting cultured hepatocytes with testosterone in the presence and absence of a candidate modulator and assessing the ability of the modulator to inhibit hepatic metabolism of the testosterone. The effects can be monitored by measuring the testosterone levels over time to measure loss or by monitoring the formation of testosterone metabolites (e.g., DHT) over time to measure degradation. In some embodiments, the testosterone is labeled (e.g., radiolabeled) to simplify its measurement.

In aspects of the invention wherein the modulator is an inhibitor of 5-α reductase, the reductase inhibitor activity of the modulator may be measured as known to one of ordinary skill in the art. In particular, inhibitors may be evaluated in vivo using a chronic rat model. (Brooks, J. R. et al., *Steroids*, 47, 1 (1986)). The chronic model utilizes castrated male rats that are dosed daily with testosterone subcutaneously and with test compound or vehicle orally for 7 days. The animals are then sacrificed and their prostates weighed. Reduction in the size of testosterone-stimulated prostate weight demonstrates activity of the test compound. Known steroid 5α-reductase inhibitors can be tested in parallel to ensure consistency of the assay method.

Candidate inhibitor modulator enzyme activities may also be determined using microsomes derived from prostate tissue as from benign prostatic hyperplasia patients, or recombinant baculovirus infected SF9 cells that express human type 1 or type 2 5α-reductase. The microsomes can be readily prepared by homogenization of the tissue or cells with differential centrifugation of the homogenate. Microsome extracts can be incubated with varying concentrations of [1,2,6,7-$^3$ H]-testosterone, 1 mM NADPH, and varying amounts of the test compounds, in a suitable buffer having a a NADPH regenerating system to maintain the NADPH concentration for the duration of the assay. Corresponding incubations can be carried out with no test compound or vehicle only group as a control study.

To conduct $IC_{50}$ measurements for 5-α-reductase type 1, assay components except testosterone can be preincubated for 10 minutes at pH 7.0 before adding 100 nM testosterone and allowing the enzymatic reaction to proceed for about 10–120 minutes. To conduct $IC_{50}$ measurements for 5-α-reductase type 2, assay components except testosterone can be preincubated for 20 minutes at pH 6.0, before adding 8 nM testosterone and allowing the enzymatic reaction to proceed for 20–40 minutes. The percentage of conversion of testosterone to DHT in the presence of test compounds compared to the corresponding conversion in the control study can be estimated using high performance liquid chromatography (HPLC) with radiochemical detection.

Methods of Measuring Serum Testosterone and DHT Levels

Methods of measuring total, free, bioavailable, and SHBG-bound testosterone and DHT levels are well known to one of ordinary skill in the art. For example, even the very low free and bioavailable serum testosterone levels in women can be measured by the method set forth by Sinha-Hikim et al., The Use of a Sensitive Equilibrium Dialysis Method for the Measurement of Free Testosterone Levels in Healthy, Cycling Women and in HIV-Infected Women, *Clinical Endocrinology and Metabolism* 83J:1312–18. (1998). This reference is specifically incorporated by reference in its entirety with respect to such methods. Other methods of measuring DHT and testosterone are set forth in the examples.

Methods of Administration and Pharmaceutical Formulations

Administration. An improved method of androgen therapy is provided by administering 1) a modulator of testosterone bioavailability and an 2) androgen selected from the group consisting of testosterone, testosterone esters, and testosterone precursors in which the androgen is orally administered in an oil vehicle or carrier suitable for human consumption (e.g., a fish oil, vegetable oil, mineral oil, FDA approved oil). In some embodiments, the modulator is a compound of formula I as set forth above. For example, the modulator can be finasteride or dutasteride or pharmaceutically acceptable salts thereof. Suitable androgens include, but are not limited to, testosterone, testosterone propionate, testosterone enanthate, testosterone cypionate, testosterone undecanoate. For the sake of convenience, the androgen and modulator can be each administered once a day. This once a day administration may preferably in the morning so as to more closely follow the normal diurnal pattern of testosterone levels in serum. The modulator may be administered separately from the androgen or co-formulated with the androgen. When administered separately the modulator may be administered before or shortly after the androgen or concurrently. A preferred route of administration for the modulator is oral and a preferred time for administration of the modulator is about the same time (e.g., within minutes) as the androgen is administered or shortly before (e.g., within the hour) the androgen is administered. For convenience and to more closely match the diurnal variation in serum testosterone levels, a preferred time for administration of the androgen and the modulator is in the morning (e.g., upon rising or with breakfast). Alternatively, the modulator, in accord with its own pharmacokinetic profile and dose response relations for modulation, may be administered at time intervals and with a frequency sufficient to maintain its modulatory activity on testosterone bioavailability as well as any 5-alpha reductase activity.

The modulator and said androgen can be administered at or about the same time or at different times. Typically, the modulator can be administered before or concurrently with the androgen. The subject can be a male or female in need of androgen therapy for any one or more of the conditions or benefits set forth in relationship to androgen therapy or androgen replacement therapy. For instance, the subject can be a male with hypogonadism. The subject can be a female lacking ovaries or having adrenal insufficiency. The treatment can also be directed toward treatment of particular health or disease conditions, for instance, osteoporosis, muscle weakness, or a reduced libido. The therapy can treat the state of testosterone deficiency itself. For instance, the treatment can be directed toward treating an adult male subject having a total serum testosterone levels below 12 nmol/liter.

In general, the amount of the modulator or androgen required to be effective varies with the subject and is ultimately at the discretion of the practitioner. The factors to be considered include the condition being treated, the route of administration, the nature of the formulation, the subject's body weight, surface area, age, gender, general condition, and/or the degree of testosterone deficiency, as well as the particular modulator to be administered. The total daily dose of each agent may be given independently as a single dose, multiple doses, e.g., two, three, four or six times per day. The individual doses may be varied so as to provide a closer approximation of the diurnal testosterone rhythm.

An objective of treatment can be to restore serum testosterone levels toward the normal testosterone profile for a person of the same age and gender. In males, androgen may be administered in daily amounts from 50 mg to 800 mg or 200 to 800 mg and the modulator is administered in an amount capable of increasing the bioavailability of the administered testosterone or testosterone ester by at least 30%, or more preferably 50 or 75%. One advantage of the present invention is the ability to achieve sustained total serum testosterone levels in the therapeutic range with the administration of comparatively low daily amounts of the androgen. For instance, the androgen can be administered in an amount from about 100 to 400 mg per daily dosage, 50 to 200 mg per daily dosage, or from 25 to 100 mg per daily dosage, or 25 to 75 mg per daily dosage. The dosage alternatively can be tailored with monitoring to keep the serum testosterone levels within a therapeutic range as known to one of ordinary skill in the art. Where the modulator of the androgen therapy is dutasteride, the modulator may be administered in an amount from 0.05 to 20 mg per daily dosage. Wherein the modulator of the androgen therapy is finasteride, the modulator may be administered in an amount from 0.1 to 40 mg per daily dosage.

Androgen replacement therapy can be directed toward a human male (e.g., an adult male or pubescent male) whose total serum testosterone levels before said therapy were found to be below 12 nmol/liter or below. In such males, the androgen (e.g., testosterone or testosterone ester) can be administered in a daily amount of up to 400 mg or higher; and the modulator (e.g., finasteride or dutasteride) administered to increase the subject's serum testosterone levels to a therapeutic level.

When treating men or women, the dosages of the androgen and modulator may be adjusted according to the serum testosterone levels achieved and/or according to the degree of the therapeutic response as ascertained by the caring physician.

Modulator formulations. The modulator to be used in the androgen therapy or androgen replacement therapy may be administered by any route and formulation as known in the art such as, for example, oral or rectal, parenteral, intraperitoneal, intravenous, subcutaneous, transdermal, subdermal, intranasal, or intramuscular. (see, for instance, Remington's Pharmaceutical Sciences, 17th Edition, (Gennaro et al. Eds., Mack Publishing Co., 1985). An appropriate amount or dose of the modulator may be determined empirically as is known in the art. An effective amount of the modulator is one which increases the bioavailability of the orally administered androgens. In some embodiments, for convenience, the modulator and androgen are administered at about the same time or combined in a single pharmaceutical formulation based on an oil carrier.

The present invention may further include flavorings and colorings to increase consumer appeal and to mask any unpleasant tastes of the composition.

Guidance for making separate modulator formulations (i.e., modulator formulations lacking the androgen) may be found in Remingtons Pharmaceutical Sciences, 20th Ed., Lippincott Williams & Wilkins., 2000; the Unites States Pharmacopeia/National Formulary, Edited and Published by, and Available from: United States Pharmacopeial Convention, Inc., 12601 Twinbrook Parkway, Rockville, Md. 20852; and Goodman and Gillmans, The Pharmacological basis for Therapeutics (10th Edition)(2001) (McGraw Hill Publishers) the contents of which are hereby incorporated by reference.

Usually the separate modulator formulations of the present invention for medical use comprise the modulator together with pharmaceutically acceptable excipients. The modulator formulations include those suitable for oral, rectal, topical or parenteral (including subcutaneous, intramuscular and intravenous) administration. Preferred are those suitable for oral administration. The modulator formulations may be in unit dosage form and may be prepared by any of the methods well known in the art of pharmacy. Modulator formulations of the present invention suitable for oral administration may be presented as discrete units (e.g., capsules, cachets, tablets or lozenges which comprise a predetermined amount of the modulator); as a powder or granules; or a suspension or solution in an aqueous liquid or non-aqueous liquid such as a syrup, elixir, or emulsion. In addition, the modulator formulations for use according to this invention may further include one or more optional accessory ingredient(s) utilized in the art of pharmaceutical formulations, e.g., diluents, buffers, flavoring agents, binders, surface active agents, thickeners, lubricants, suspending agents, preservatives (including antioxidants) and the like.

Androgen formulations. Methods of formulating lipophilic hormones in oil vehicles are well known to one of ordinary skill in the art. The androgen can be suspended or dissolved in any pharmaceutically suitable oil vehicle which may be a liquid or semi-liquid solution, suspension, or emulsion. Oils can be used with or without the addition of a solubilizer, a surfactant, a suspending agent or emulsifier. Examples of oils that are used are olive oil, peanut oil, cottonseed oil, soybean oil, castor oil and sesame oil. Preferred oils include fish, vegetable, and mineral oils as set forth above. In some embodiments, in view of the health benefits conferred by their omega fatty acid content, oils rich in the omega-3 fatty acids or their precursors may be used (e.g., fish oils such as salmon or tuna oils or vegetable oils such as flax seed or grape seed oils may be used. Preparation of testosterone and testosterone ester formulations in sesame oil is described in Example 2 below. The oil may comprise oil soluble antioxidants such as Vitamin E. Additional excipients such as benzyl benzoate, benzyl alcohol and ethanol may also be used. To facilitate ingestion of the liquid and its delivery to the stomach, the oil may sealed in capsules (e.g., soft gel capsule, or hard shell capsules).

For example, micronized testosterone enanthate can be suspended in distilled natural fish oil at a concentration of 400 mg/ml and mixed for a period of time sufficient to make a homogeneous emulsion which can then be encapsulated in a fixed volume to provide a unit dose format or else the emulsion can be placed in a container and measured out to be mixed and served with food (e.g., milk).

In some embodiments, the modulator is co-formulated with the androgen in an oil vehicle formulated for oral administration. A micronized modulator may be co-formulated with the androgen. For instance, 100 mg dutasteride and 40 g micronized testosterone enanthate can be suspended in 100 ml distilled natural fish oil and mixed for a period of time sufficient to make a homogeneous emulsion which can then be encapsulated in a fixed volume (e.g., 0.5, 1.0, 2.0 ml) to provide a unit dose or else the combination emulsion can be placed in a container and measured out in volumes, for instance, of 0.5 ml. 1.0 ml, or 2.0 ml to be mixed and served with food (e.g., milk).

Guidance in making androgen formulations (with and without the modulator) can be found in Remingtons Pharmaceutical Sciences, 20th Ed., Lippincott Williams & Wilkins., 2000; the United States Pharmacopeia/National Formulary, Edited and Published by, and Available from: United States Pharmacopeial Convention, Inc., 12601 Twinbrook Parkway, Rockville, Md. 20852; and Goodman and Gilmans, The Pharmacological basis for Therapeutics (10th Edition)(2001) (McGraw Hill Publishers) the contents of which are hereby incorporated by reference.

U.S. Pat. No. 6,652,880 and U.S. Pat. No. 6,096,338 also disclose synthetic oil vehicle formulations for the oral administration of testosterone, testosterone esters, or testosterone precursors. These references are incorporated by reference herein in their entirety with respect to the pharmaceutically acceptable carriers and excipients disclosed therein. For instance, a formulation can comprise a digestible lipid substance and optionally a pharmaceutically acceptable surfactant for dispersing the substance in vivo after administration. The surfactant can have a hydrophilic surfactant component that does not substantially interfere with the digestion of the oil. Suitable digestible lipid substances can include complete or partial esters of medium chain (C8–C12) or long-chain (C14–C22) fatty acids with low molecular weight (up to C6) mono-, di- or polyhydric alcohols. Medium chain length triglycerides or long chain tri- and diglyceride mixtures which may contain monoglycerides may also be used. See, Lacy et al. in Patent Cooperation Treaty WO 95/24893 published Sep. 21, 1995, which is incorporated by reference with respect to the pharmaceutically acceptable carriers and excipients disclosed therein. The lipophilic surfactants used include, but are not limited to, fatty acids; mono- and/or diglycerides of fatty acids; acetic, succinic, lactic, citric and/or tartaric esters of mono and/or diglycerides of fatty acids; propylene glycol mono- and/or di-esters of fatty acids; polyglycerol esters of fatty acids; castor oil ethoxylates; acid and ester ethoxylates; and sorbitan esters of fatty acids. The hydrophilic surfactants when used preferably have a hydrophilic/lipophilic balance (HLB) value greater than 10 and include phospholipid; polyoxyethylene sorbitan fatty acid derivatives; castor oil or hydrogenated castor oil ethoxylates; fatty acid ethoxylates; alcohol ethoxylates; polyoxyethylene, polyoxypropylene co-polymers and block co-polymers; anionic surfactants and alkylphenol surfactants. The formulations may contain ethanol as a co-solvent and formulations containing up to 15% by weight ethanol are disclosed.

General procedures for making oral dosage forms are described in Pharmaceutical Dosage Forms and Drug Delivery Systems, 6.sup.th Ed. (H. C. Ansel, N. G. Popovich and L. V. Allen, Eds., Williams & Wilkins (1995)), which is incorporated by reference herein. Other procedures are disclosed in Pharmaceutical Dosage Forms: Disperse Systems, Vol. 2, 2.sup.nd Ed. (H. A. Lieberman, L. Lachman and J. B. Schwartz, Eds. (1996)), which are incorporated by reference herein.

The testosterone, testosterone ester, or testosterone precursor may be formulated in a digestible oil selected from triglycerides or propylene glycol esters of medium chain length (C8–C12) and/or long chain length (C13–C22) fatty acids; propylene glycol monolaurate (lauroglycol), a lipophilic surfactant which comprises a glyceride of a C5 to C10 fatty acid; and a hydrophilic surfactant which is a polyoxyethylene hydrogenated castor oil.

The pharmaceutically acceptable oil vehicle for the testosterone, testosterone ester, or testosterone precursor may comprise (1) the vegetable and animal oils; (2) and fats consisting of mono-, di- and triglycerides of various fatty acids or containing these glycerides as primary constituent; (3) fatty acid esters or alcohols, higher aliphatic alcohols; (4) saturated or unsaturated fatty acids, higher aliphatic alcohols; (5) the mono-, di and triglyceride oils and glycerol ethers; (6) certain types of wax or (7) mixture of the above. The preparation may be preferably liquid or semi-liquid at ambient temperature, that is, at a temperature in the range of about 10° C. to about 30° C. The testosterone, testosterone ester, or testosterone precursor can be dissolved in the substance and the solution processed in the preparation or processed to a pharmaceutical dosage unit form. Optionally, part of the testosterone, testosterone ester, or testosterone precursor is present in the liquid lipoid in suspended form at ambient temperature, whereby the quantities of esters and lipoid substance have preferably been correlated such that the ester is fully dissolved in the carrier at body-temperature. See U.S. Pat. No. 4,147,783 which is incorporated by reference in its entirety with respect to the androgen formulations disclosed therein. The above pharmaceutical composition may be formulated as soft gelatine capsules or microcapsules.

EXAMPLES

The following examples are offered to illustrate, but not to limit the claimed invention.

Example 1

Example 1 presents the results of an open-label, single-dose pharmacokinetic study of oral administration of 400 mg doses of testosterone in normal men whose endogenous testosterone production has been temporarily suppressed by the administration of the potent GnRH antagonist acyline, previously shown to be safe and effective at suppressing endogenous testosterone production in men for 2 weeks (see Herbst K L et al, *J Clin Endocrinol Metab* 87:3215–3220 (2002) and Herbst K L, et al. JCEM (in press)). The study examined the impact of concomitant administration of the 5-α-reductase inhibitors dutasteride and finasteride on serum testosterone levels, and also the impact of food on testosterone absorption.

Subjects: Eight healthy, normal male volunteers aged 18–50 were enrolled. "Normality" was determined by a normal medical history and physical examination; no medications being taken other than study drugs and normal values on routine hematology, blood chemistry and liver function tests. Subjects were not be eligible for participation in this study if they demonstrated abnormal reproductive hormone levels (LH, FSH or testosterone), or showed evidence of underlying disease (based on results of the physical exam and the routine labs). Additional exclusion criteria included any history or evidence of significant chronic or acute medical illness, previous or current ethanol or anabolic steroid abuse. Subjects were recruited through local news media (newspaper and radio) and college campus bulletin boards. University of Washington Investigational Review Board approval was obtained before subject enrollment.

Study Design. The study was divided into a screening period, a two-week drug exposure period, and a one-month recovery period (see FIG. 1, Experimental Design). At screening, study investigators performed an interview and physical examination; blood samples for measurement of hormones (testosterone, DHT, Estradiol (E2), FSH and LH), routine hematology, chemistry and hepatic function tests were collected. No drugs were administered in the control period.

Following the control period, subjects underwent the following treatment: (Day 0) Acyline 300 μg/kg once, followed 24 hours later (Day 1) by testosterone 400 mg po once, with breakfast, followed 24 hours later (day 2) by finasteride 5 mg po mg po bid, followed 24 hours later (day 3) by finasteride 5 mg and 30 minutes later testosterone 400 mg po once, given while fasting, followed 24 hours later (Day 4) by finasteride 5 mg po once, then 30 minutes later testosterone 400 mg po once with food. Subjects will come in on day 5 for a brief blood draw. There was no drug administration on days 5 or 6. On day 7, subjects took dutasteride 0.5 mg po bid, then on day 8 then took dutasteride 0.5 mg once, then 30 minutes later received 400 mg po once while fasting, followed 24 hours later (Day 9) by dutasteride 0.5 mg po once, followed 24 hours later (day 10) by dutasteride 0.5 mg po once followed 30 minutes later by T 400 mg po once, given with breakfast, on day 11 subjects came in for an early morning blood draw only.

In other words: the study protocol was

Day

M Day 0: Acyline 300 ug/kg by subcutaneous injection (60 minutes)

Tu Day 1: oral T 400 mg by mouth, with breakfast, 12-hour blood draws

W Day 2: Blood draw, then finasteride 5 mg po bid (15 minutes)

T Day 3: Finasteride 5 mg po, then oral T 400 mg by mouth, no food for 90 minutes 12-hour blood draws F Day 4; Finasteride 5 mg po, then oral T 400 mg by mouth, with breakfast 12-hour blood draws S Day 5, AM blood draw (15 minutes)

S Day 6, day off

M Day 7, AM blood draw, then dutasteride 0.5 mg po bid (15 minutes)

Tu Day 8, Dutasteride 0.5 mg po, then oral T 400 mg by mouth, no food for 90 min 12-hour blood draws W Day 9, AM blood draw, then Dutasteride 0.5 mg po. (15 minutes)

T Day 10, Dutasteride 0.5 mg po, then oral T 400 mg by mouth with breakfast 12-hour blood draws F Day 11, AM blood draw (15 minutes)—end of study period.

The administration of the testosterone on day 3 and 8 took place while the subjects were fasting and they did not eat any food for 90 minutes after the administration of the oral testosterone. The administration of the testosterone on days 1, 4 and 10 took place while the subjects were eating breakfast with at least 15 grams of fat.

During treatment on days 1, 3, 4, 8 and 10 prior to androgen dosing subjects had blood drawn for testosterone, DHT, E2, creatinine, AST and ALT. After drug dosing subjects had blood drawn at 30 minutes, 1, 2, 3, 4, 6, 8, 10, 12 hours for serum T, DHT and E2. After treatment day 11, subjects underwent a final assessment on day 28–42.

Acyline (IND #53,539), manufactured by Multiple Peptide Systems, San Diego, Calif. and supplied by the National Institute of Child Health and Human Development (NICHD) was used.

Figure 2B:
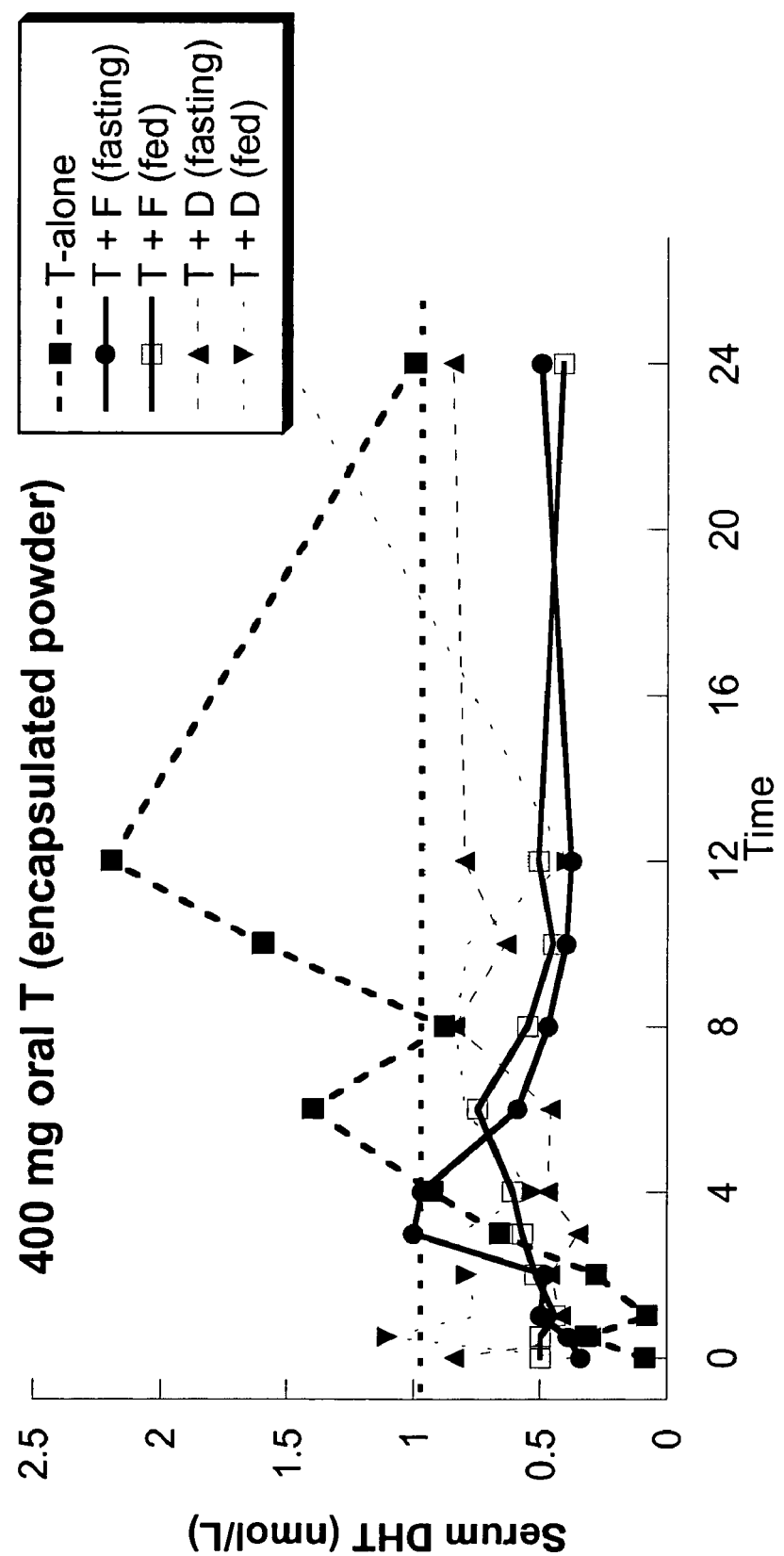
Figure 3A:
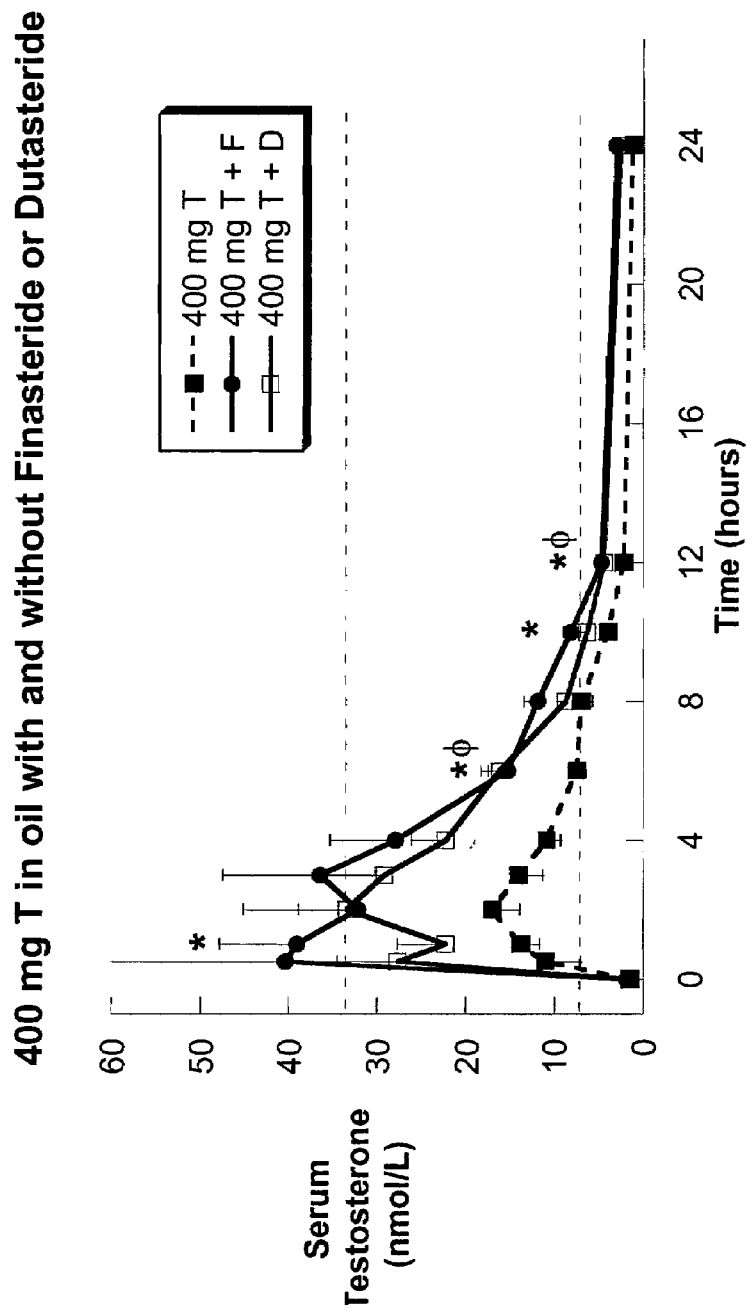
FIG. 3. Effect of dutasteride and finasteride administration on mean serum testosterone levels (FIG. 3A) and DHT levels (FIG. 3B) in men orally administered testosterone in the sesame oil vehicle per the protocol of FIG. 1.
Figure 3B:
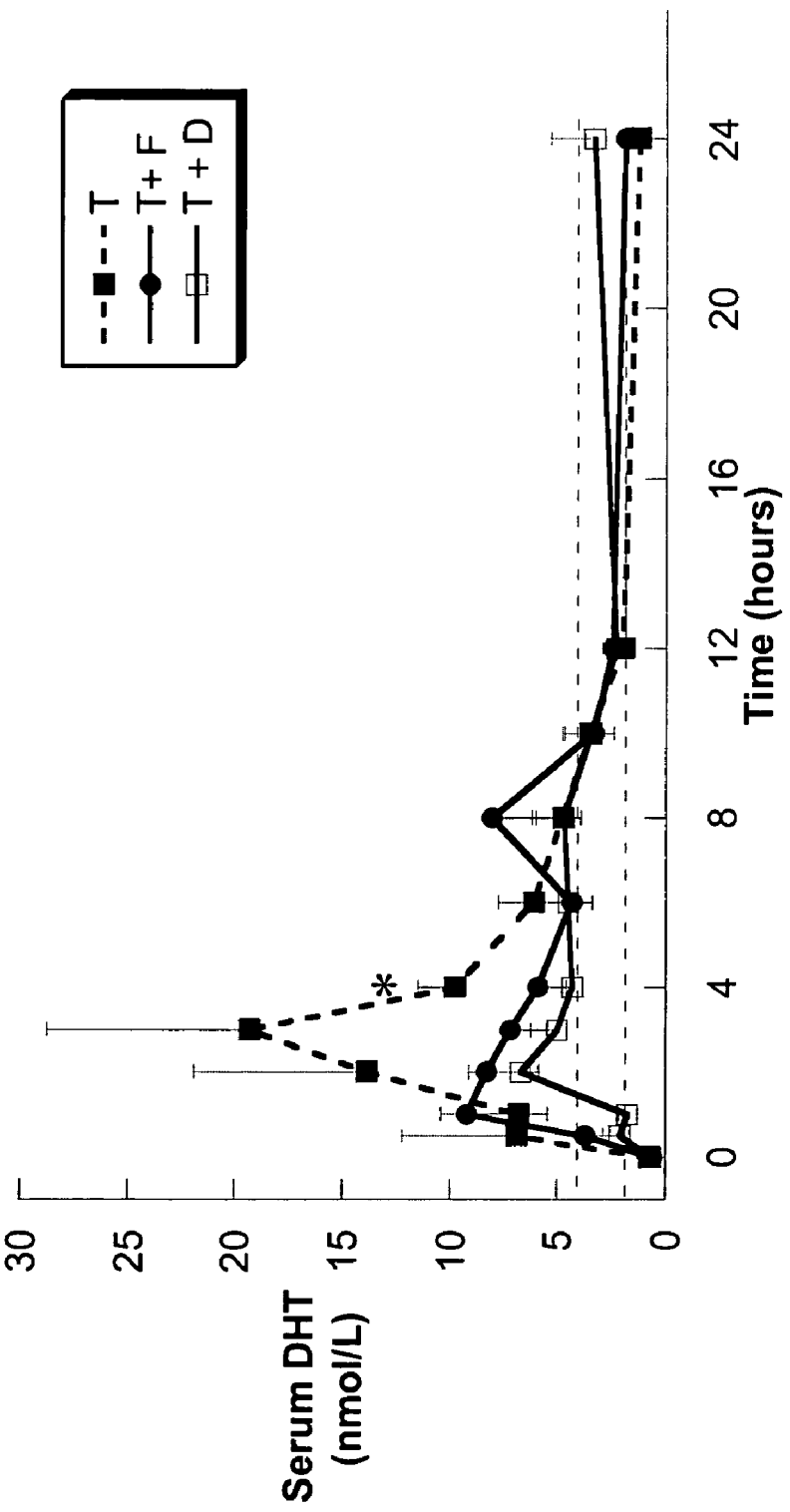
Figure 4:
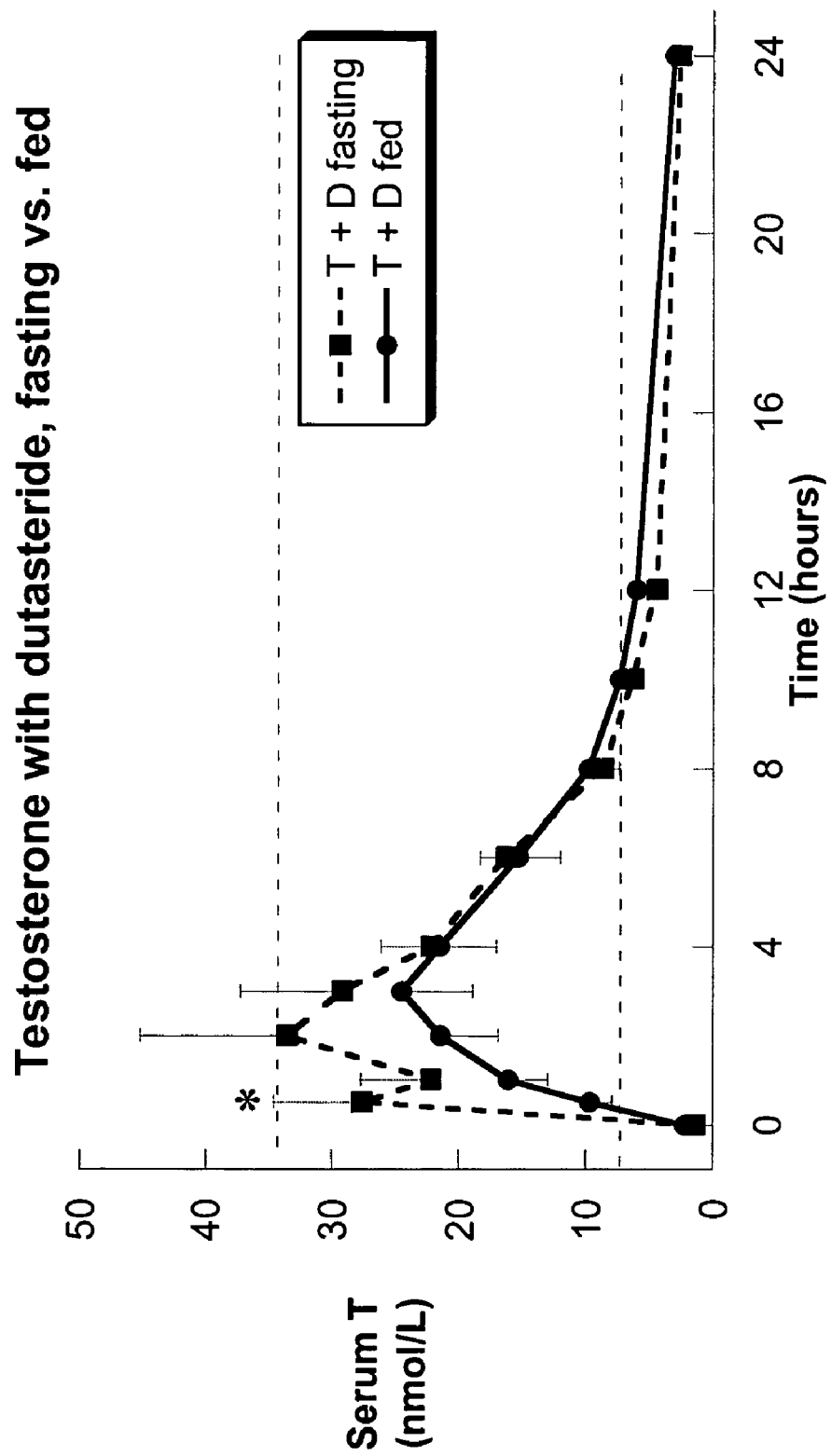
FIG. 4. Effect of dutasteride on mean serum testosterone levels in fasting and fed men orally administered testosterone in the sesame oil vehicle per the protocol of FIG. 1.
Figure 5:
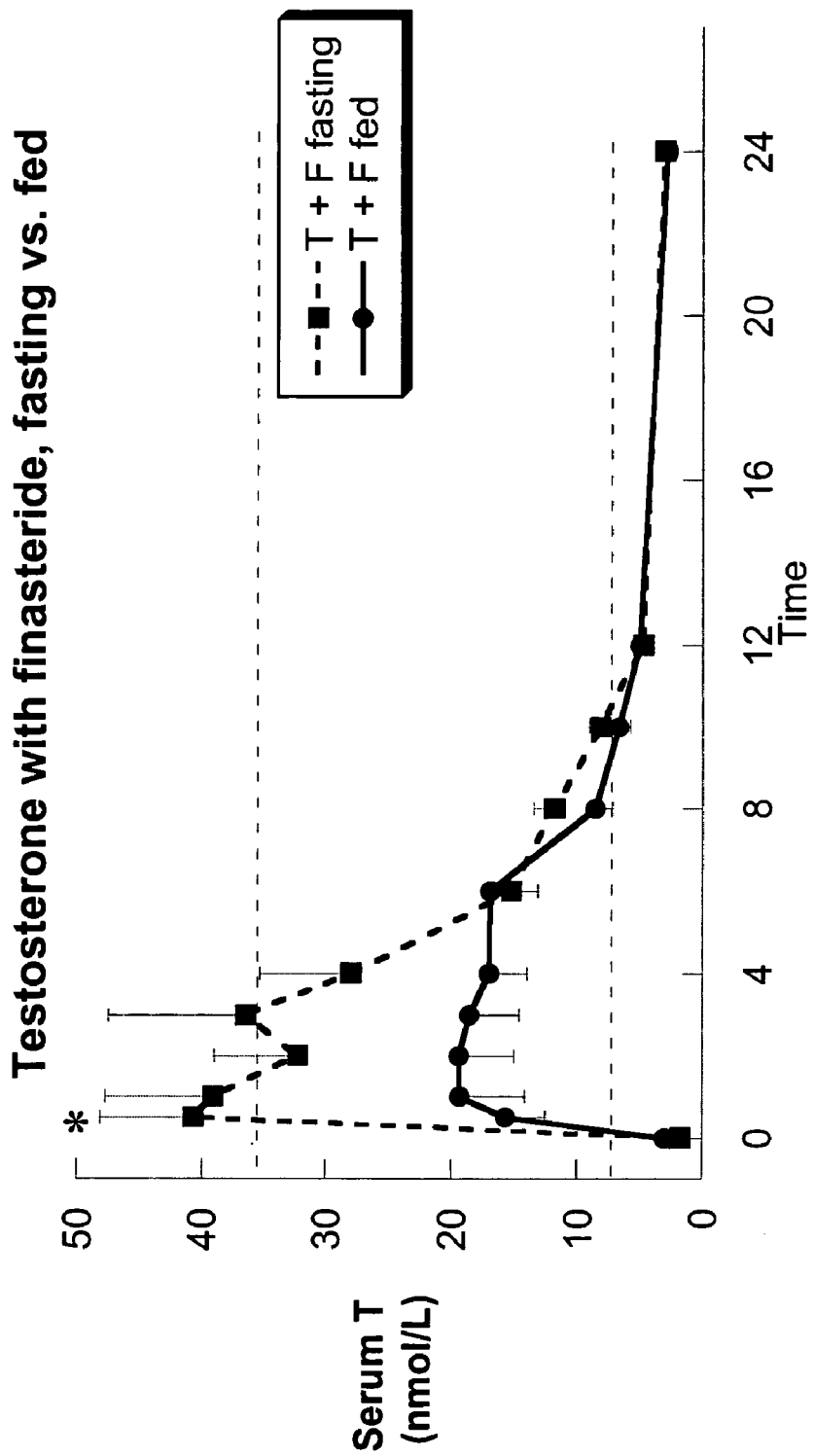
FIG. 5. Effect of finasteride on mean serum testosterone levels in fasting and fed men orally administered testosterone in the sesame oil vehicle per the protocol of FIG. 1.

The study design was directed toward determining the single-dose pharmnacokinetics of a 400 mg dose of oral testosterone alone, with two different 5a reductase inhibitors and what, if any, the effect of food is on absorption of orally administered T. FIG. 2 shows the inability of dutasteride or finasteride to increase the bioavailability of testosterone administered in encapsulated form by the oral route for either fasting or fed men. FIG. 3 shows the ability of dutasteride and finasteride to increase the bioavailability of testosterone to increase the bioavailability of testosterone administered in sesame oil by the oral route. FIGS. 4 and 5, when compared to FIG. 3, shows the ability of dutasteride and finasteride, respectively, to increase the bioavailability of testosterone orally administered in sesame oil for both fasting and fed men.

Example 2

Example 2 relates to FIGS. 6–11 and illustrates the effects of orally administered dutasteride on the pharmacokinetics and bioavailability of single oral doses of testosterone and testosterone enanthate with and without the concomitant administration of dutasteride. The study also illustrates the pharmacokinetics and safety of single high-doses oral testosterone in oil in healthy men rendered temporarily hypogonadal by treatment with a GNRH antagonist.

Subjects: Fourteen healthy, normal male volunteers between 18 and 45 years of age were recruited through local news media (newspaper and radio) and college campus bulletin boards and enrolled. The inclusion criteria were: no prior medical illnesses, normal physical examination, routine hematology, blood chemistry and liver function. Exclusion criteria included: regular use of any medication, abnormal serum testosterone , DHT, estradiol (E2), or previous or current ethanol, illicit drug or anabolic steroid abuse. A total of 16 men were evaluated for eligibility. Of, these 14 men were potentially eligible and agreed to participate in the study. The two men who did not enroll in the study were excluded for elevated bilirubin (one subject), and use of finasteride (for the treatment of male pattern baldness). One enrolled subject failed to appear for his acyline injection and was therefore not studied further. The institutional review board of the University of Washington approved all study procedures, and subjects gave written informed consent before screening.

Study Design: Participants were randomly assigned to one of two groups: 1) oral testosterone in sesame oil, or 2) oral testosterone enanthate in sesame oil (Delatestryl, BTG Pharmaceuticals, Iselin, N.J.) at a concentration of 200 mg/ml. A sample size of seven subjects per group was estimated to have an 80% power with an α of 0.05 to detect a 50% in the change in serum testosterone area-under-the curve between doses. The oral testosterone enanthate in sesame oil was manufactured by the compounding pharmacy at the University of Washington. Briefly, micronized testosterone (U.S.P. grade, Spectrum Quality Projects, Gardena, Calif., USA) was suspended at 100 mg/ml in sesame oil (N.F. grade, Spectrum Quality Projects, Gardena, Calif., USA), and mixed thoroughly on a magnetic stir plate to create a homogenous testosterone enanthate/sesame oil emulsion. The compounding pharmacist then drew up the emulsion into syringes at the desired dose levels (200, 400 and 800 mg). The dose of oral testosterone enanthate in sesame oil was normalized for the testosterone content, so that the subjects in the testosterone enanthate group (molecular weight 397) were administered 276, 554 and 1108 mg of testosterone enanthate, corresponding to 200, 400 and 800 mg of testosterone.

Figure 6:
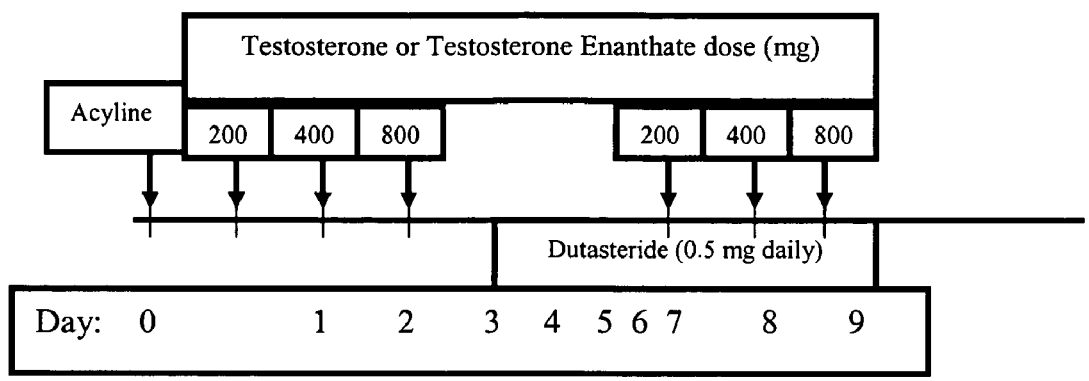
FIG. 6. Study Design. Participants were randomly assigned to one of two groups: 1) oral testosterone in sesame oil, or 2) oral testosterone enanthate in sesame oil (Delatestryl, BTG Pharmaceuticals, Iselin, N.J.) at a concentration of 200 mg/ml. The drug exposure period lasted 12 days as depicted. On day 0, subjects received a single injection of the GnRH antagonist acyline (300 mcg/kg SQ), which has been shown to suppress testosterone production in normal men for a minimum of 15 days (29 and K. Herbst, personal communication). One, two and three days after acyline administration, subjects drank 200, 400 or 800 mg of testosterone or testosterone enanthate in oil, mixed with 8 oz of whole milk. These doses were repeated days eight, nine and ten days after the acyline injection. Subjects self-administered dutasteride (0.5 mg po once daily) on days 5–10 after the acyline injection. For safety, subjects underwent daily testing of liver function (AST, bilirubin, alkaline phosphatase), kidney function (BUN, creatinine) and hematopoiesis (hemoglobin and hematocrit).
Figure 8:
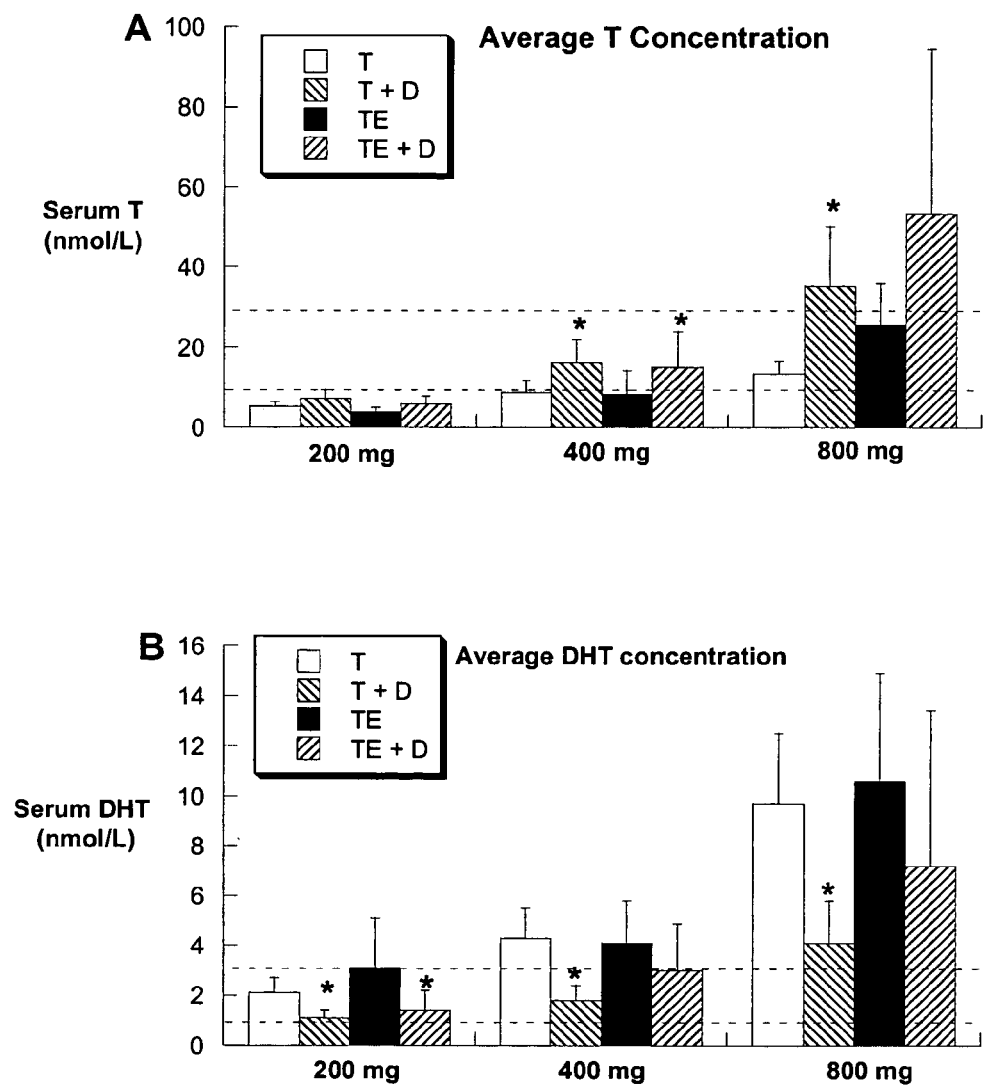
FIG. 8. Mean average concentration of serum testosterone (A) and dihydrotestosterone (B) over the 24-hour interval after oral dosing. The dotted lines represent the upper and lower limits of the normal range for serum testosterone. *$P<0.05$ compared with testosterone alone.

The drug exposure period lasted 12 days (FIG. 6). On day 0, subjects received a single injection of the GnRH antagonist acyline (300 mcg/kg SQ), which has been shown to suppress testosterone production in normal men for a minimum of 15 days (29 and K. Herbst, personal communication). One, two and three days after acyline administration, as per the protocol of FIG. 6, subjects drank 200, 400 or 800 mg of testosterone or testosterone enthanate in oil, mixed with 8 oz of whole milk. These doses were repeated days eight, nine and ten days after the acyline injection. Subjects self-administered dutasteride (0.5 mg po once daily) on days 5–10 after the acyline injection. For safety, subjects underwent daily testing of liver function (AST, bilirubin, alkaline phosphatase), kidney function (BUN, creatinine) and hematopoiesis (hemoglobin and hematocrit).

Measurements: After dosing on day 1, 2, 3, 8, 9 and 10, subjects had blood drawn via an heparin-locked iv line 30 minutes, 1, 2, 4, 6, 8, 10, 12 and 24 hours for measurement of serum testosterone, DHT and SHBG. Total serum testosterone was measured by a radioimmunoassay (Diagnostic Products Corporation, Los Angeles, Calif.). The assay had a sensitivity of 0.35 nmol/L and interassay variations for low, mid and high pools of 13.6%, 6.1%, 6.8%, and intra-assay variation of 10.0%, 5.3%, 6.6%. The normal range was 8.7–33 nmol/L. DHT was measured using an RIA Kit (Diagnostic Systems Laboratory, Los Angeles, Calif.). The sensitivity of this assay was 0.043 nmol/L and the intra-assay variation for mid and low-range pools was 9.9% and 11%, with interassay coefficients of variations of 19 and 25%. The normal range for serum DHT was 1.0–2.9 nmol/L. SHBG was measured by an RIA (Delphia, Wallac Oy, Turku, Finland). The sensitivity of this assay was 0.2 mnol/L and the interassay variation for low, mid and high pools was 31%, 10.6%, 6.8%, and the intra-assay variation was 3.8%, 1.7%, 2.2%. The normal range was 3.2–47 nmol/L. The normal ranges for testosterone, DHT and SHBG were determined in our laboratory using serum samples obtained from 100 normal men aged 20–50 years.

Statistics: Hormone were log transformed prior to analysis. Average concentration during the 24 hour period after dosing (Cavg), maximum concentration after dosing (Cmax), time to maximum concentration (Tmax), area-under-the curve (AUC) and elimination phase half-life ($T_{1/2}$) were calculated using a pharmacokinetics program (PK solutions, Golden, Colo.). Hormone levels and pharmacokinetic parameters between successive doses of testosterone or testosterone enanthate with or without dutasteride were compared by paired testosterone-tests with a Bonferroni correction for repeated measures. Changes between groups were analyzed by ANOVA. Statistical analyses were performed using STATA (College Park, Tex., USA). Type I error was set at 0.05 for all analyses.

Results: Fourteen men were enrolled in the study, seven were randomized to the testosterone group and seven were randomized to the testosterone enanthate group. There were no significant baseline differences between the groups in any characteristic (Table 1). Excepting the subject who failed to appear for his acyline injection, all subjects completed the drug exposure period. There were no significant adverse effects during the study. More than half of the subjects experienced transient pruritis at the site of the acyline injection, which resolved in all cases within one hour of the injection. Eight subjects complained of mild, transient "hot flash" symptoms towards the end of the study period presumably due to low testosterone levels; however, no subject complained of feelings of anger, aggression or irritability during treatment. One subject developed a small area of gynecomastia (less than 1×1 cm) immediately under the nipple develop during the treatment period, but this resolved during follow-up. There were no changes seen in serum markers of liver or kidney function, or in the hematocrit or hemoglobin during the treatment phase or at follow-up. Furthermore, no significant changes in blood pressure or pulse were observed. Testosterone and gonadotropin levels returned to baseline in all subjects during the follow-up period (data not shown). No subjects were lost to follow-up.

TABLE 1

Baseline characteristics of study subjects by group (means ±SD)

|  | T group (N = 7) | TE group (N = 6) | P-value |
|---|---|---|---|
| Age (years) | 24.2 ± 8.7 | 24.7 ± 6.7 | 0.93 |
| Weight (kg) | 77 ± 4.0 | 89 ± 16 | 0.08 |
| Height (cm) | 182 ± 9 | 186 ± 11 | 0.51 |
| BMI (kg/m$^2$) | 23.3 ± 2.3 | 25.8 ± 4.2 | 0.21 |
| Total testosterone (nmol/L) | 22.7 ± 8.0 | 17.0 ± 5.8 | 0.17 |
| Dihydrotestosterone (nmol/L) | 1.24 ± 0.46 | 1.1 ± 0.5 | 0.46 |
| Estradiol (pmol/L) | 251 ± 73 | 240 ± 46 | 0.74 |

TABLE 1-continued

Baseline characteristics of study subjects by group (means ±SD)

|  | T group (N = 7) | TE group (N = 6) | P-value |
|---|---|---|---|
| SHBG (nmol/L) | 33.2 ± 9.84 | 24.0 ± 10.7 | 0.78 |
| Free Testosterone (pmol/L) | 435 ± 156 | 341 ± 92 | 0.32 |

Serum Testosterone: All subjects were suppressed to castrate levels of testosterone by 24 hours after acyline adminstration (day zero: testosterone 20.0±7.4 nmol/L vs. 2.3±0.5 nmol/L (day one); P<0.0001). There was no difference in the serum testosterone levels 24-hours post acyline between groups: [2.3±0.7 (testosterone ) vs. 2.3±0.8 (testosterone enanthate), P=0.9].

With the administration of both oral testosterone and oral testosterone enanthate in oil, serum testosterone was significantly increased in all men in a dose-dependent fashion (FIGS. 7A–C). In addition, the maximum concentrations of testosterone , average concentrations of serum testosterone and area under the curve of serum testosterone increased significantly in a dose-dependent fashion (Table II, FIG. 8A), with the maximum concentration of testosterone after oil dosing exceeding the normal range for the 800 mg dose of testosterone and the 400 and 800 mg doses of oral testosterone enanthate in oil. The time of maximum concentration was between 2.5 and 4.5 hours in all cases, and the calculated terminal half-line of oral testosterone and testosterone enanthate in oil was bewteen 7.5 and 11 hours.

TABLE 2

Testosterone pharmacokinetics after administration of a single dose of oral Testosterone and oral testosterone enanthate (TE) in oil with and without dutasteride to normal men previously administered a GnRH antagonist. All data are means ± SD.

|  | Dose (mg) | | | | | |
|---|---|---|---|---|---|---|
|  | 200 | 400 | 800 | 200 | 400 | 800 |
|  | Testosterone-only | | | Testosterone + Dutasteride | | |
| Testosterone (N = 7) | | | | | | |
| Cavg (nmol/L) | 5.2 ± 1.2 | 8.7 ± 3.0$^a$ | 13.4 ± 3.1$^a$ | 7.2 ± 2.1$^b$ | 16.1 ± 5.8$^{a,c}$ | 35.2 ± 15$^{a,c}$ |
| Cmax (nmol/L) | 12.3 ± 4.1 | 26.1 ± 15.1 | 40.4 ± 10.1$^a$ | 22.2 ± 8.4$^b$ | 50.3 ± 30.9$^{a,b}$ | 122.1 ± 82$^{a,b}$ |
| Tmax (hours) | 2.8 ± 1.9 | 3.9 ± 2.6 | 3.1 ± 2.0 | 3.1 ± 2.0 | 3.8 ± 3.1 | 3.4 ± 1.5 |
| AUC (nmol-hours/L) | 124 ± 28 | 208 ± 74$^a$ | 328 ± 72$^a$ | 176 ± 46$^c$ | 393 ± 140$^{a,c}$ | 846 ± 363$^{a,c}$ |
| T$_{1/2}$ (hours) | 10.4 ± 2.9 | 10.7 ± 6.0 | 8.1 ± 5.0 | 9.9 ± 3.8 | 9.0 ± 2.8 | 7.8 ± 3.2 |
|  | Testosterone Enanthate-only | | | Testosterone Enanthate + Dutasteride | | |
| T Enanthate (N = 6) | | | | | | |
| Cavg (nmol/L) | 3.8 ± 1.1 | 8.3 ± 5.9 | 25.5 ± 10.4$^{a,d}$ | 5.9 ± 1.9$^b$ | 15.0 ± 8.8$^{a,b}$ | 53.4 ± 41$^a$ |
| Cmax (nmol/L) | 14.6 ± 8.5 | 51.8 ± 59 | 160.8 ± 149 | 20.2 ± 9.4 | 74 ± 55$^a$ | 229 ± 228 |
| Tmax (hours) | 3.2 ± 2.6 | 4.1 ± 4.0 | 2.7 ± 1.5 | 4.1 ± 4.2 | 4.3 ± 3.8 | 3.3 ± 2.4 |
| AUC (nmol-hours/L) | 90 ± 27 | 200 ± 140 | 612 ± 249$^d$ | 141 ± 41 | 450 ± 196$^{a,b}$ | 1327 ± 1021 |
| T$_{1/2}$ (hours) | 10 ± 2.4 | 10 ± 3.2 | 8.4 ± 3.2 | 9.4 ± 3.2 | 9.2 ± 2.9 | 8.4 ± 2.4 |

$^a$P < 0.05 compared with immediately lower dose,
$^b$P < 0.05 compared with testosterone and testosterone enanthate-only,
$^c$P < 0.01 compared with testosterone-only,
$^d$P < 0.05 compared with testosterone-only.
Cavg = average concentration during 24-hour period after dosing;
Cmax = maximum concentration after dosing;
Tmax = time of maximum concentration:
AUC = area under-the-curve;
T$_{1/2}$ = terminal half-life Co-administration of dutasteride with oral testosterone or testosterone enanthate in oil significantly increased the resulting serum testosterone levels compared with administration of testosterone or testosterone enanthate alone (FIGS. 7C–F). The maximum concentration of testosterone after oral dosing with the combination of testosterone or testosterone enthanate and dutasteride exceeded the normal range at both the 400 and 800 mg doses for the testosterone and testosterone enanthate in oil. Similar to the administration of testosterone or testosterone enanthate-only, the time to maximum concentration remained between 2.5 and 4.5 hours and the calculated terminal half-life was between 8 and 10 hours. The testosterone area-under-the-curve for the combination of testosterone and dutasteride was significantly increased at all doses compared to testosterone alone [200 mg: 124±28 nmol-hours/L (testosterone-alone) vs. 176±45 nmol-hours/L (testosterone+D); 400 mg: 208±74 nmol-hours/L (testosterone-alone) vs. 393 nmol-hours/L (testosterone+D); 800 mg: 328±82 nmol-hours/L (testosterone-alone) vs. 846±363 nmol-hours/L (testosterone+D); P<0.01 for all comparisons].

Serum DHT levels: Serum DHT decreased significantly 24 hours after acyline adminstration [Day 0 DHT: 1.6±0.6 nmol/L vs. 0.6±0.2 nmol/L (day 1); P<0.05]. There was no difference in serum DHT levels 24-hours post acyline between groups: [0.5±0.2 (testosterone) vs. 0.6±0.2 (testosterone enanthate), P=0.63].

The administration of both oral testosterone and oral testosterone enanthate in oil significantly increased the serum DHT in all men in a dose-dependent fashion (FIGS. 9A–F). In addition, the maximum concentrations of DHT and area under the curve increased significantly (Table 3), with the maximum concentration of DHT after oral dosing exceeding the normal range for for all doses of testosterone and testosterone enanthate in oil. The time of maximum concentration was between 3.9 and 6 hours in all cases, and the calculated terminal half-line of oral testosterone and testosterone enanthate in oil was bewteen 7.5 and 11 hours.

TABLE 3

DHT pharmacokinetics after administration of a single dose of oral Testosterone and oral testosterone enanthate (TE) in oil with and without dutasteride to normal men previously administered a GnRH antagonist. All data are means ±SD.

| Dose (mg) | 200 | 400 | 800 | 200 | 400 | 800 |
|---|---|---|---|---|---|---|
| Testosterone (N = 7) | | Testosterone-only | | | Testosterone + Dutasteride | |
| Cavg (nmol/L) | 2.1 ± 0.6 | 4.3 ± 1.2[a] | 9.7 ± 2.8[a] | 1.1 ± 0.3[c] | 1.8 ± 0.6[a,c] | 4.1 ± 1.7[a,c] |
| Cmax (nmol/L) | 5.6 ± 2.0 | 12.0 ± 3.9[a] | 30.0 ± 7.0[a] | 2.2 ± 0.7[c] | 4.2 ± 1.6[a,c] | 10.3 ± 3.5[a,c] |
| Tmax (hours) | 4.7 ± 3.4 | 5.0 ± 3.8 | 3.9 ± 3.5 | 5.1 ± 3.0 | 6.0 ± 3.3 | 4.6 ± 2.2 |
| AUC (nmol-hours/L) | 51 ± 15 | 106 ± 29[a] | 239 ± 71[a] | 25 ± 8.5[b] | 45 ± 15[a,c] | 99 ± 40[a,c] |
| $T_{1/2}$ (hours) | 10 ± 2.3 | 9.3 ± 2.0 | 7.5 ± 3.6 | 9.9 ± 3.8 | 10.6 ± 2.3 | 9.9 ± 2.2 |
| Enanthate (N = 6) | | Testosterone Enanthate-only | | | Testosterone Enanthate + Dutasteride | |
| Cavg (nmol/L) | 3.1 ± 2.0 | 4.1 ± 1.7 | 10.6 ± 4.3[a] | 1.4 ± 0.8[b] | 3.0 ± 1.9[a] | 7.2 ± 6.2 |
| Cmax (nmol/L) | 15.3 ± 12 | 21.0 ± 19 | 48.8 ± 22.6[a] | 4.0 ± 2.4[b] | 8.0 ± 6.5[a] | 25.3 ± 24[b] |
| Tmax (hours) | 3.2 ± 1.3 | 4.2 ± 3.5 | 2.5 ± 1.6 | 5.5 ± 3.7 | 7.2 ± 4.0 | 2.7 ± 2.0 |
| AUC (nmol-hours/L) | 75 ± 48 | 100 ± 42 | 253 ± 101 | 35 ± 18[b] | 72 ± 45 | 173 ± 148 |
| $T_{1/2}$(hours) | 10 ± 2.2 | 9.1 ± 3.5 | 8.6 ± 2.9 | 8.6 ± 3.5 | 8.4 ± 3.4 | 9.0 ± 3.3 |

[a]P < 0.05 compared with immediately lower dose,
[b]P < 0.05 compared with testosterone and testosterone enanthate-only,
[c]P < 0.01 compared with testosterone-only,
[d]P < 0.05 compared with testosterone-only.
Cavg = average concentration during 24-hour period after dosing;
Cmax = maximum concentration after dosing;
Tmax = time of maximum concentration:
AUC = area under-the-curve;
$T_{1/2}$ = terminal half-life Co-administration of dutasteride with oral testosterone or testosterone enanthate in oil significantly decreased both maximum and aveage serum DHT levels and compared with administration of testosterone or testosterone enanthate alone (FIG. 3B and Table 3). The maximum concentration of DHT after oral dosing with the combination exceeded the normal range at the 800 mg dose for the testosterone and the 400 mg and 800 mg doses of testosterone enanthate in oil. The time to maximum concentration was between 2.5 and 7.5 hours and the calculated terminal half-life was between 8 and 10 hours. The DHT area-under-the-curve for the combination of testosterone and dutasteride was significantly decreased compared to the area-under-the-curve testosterone alone at all doses.

Figure 10:
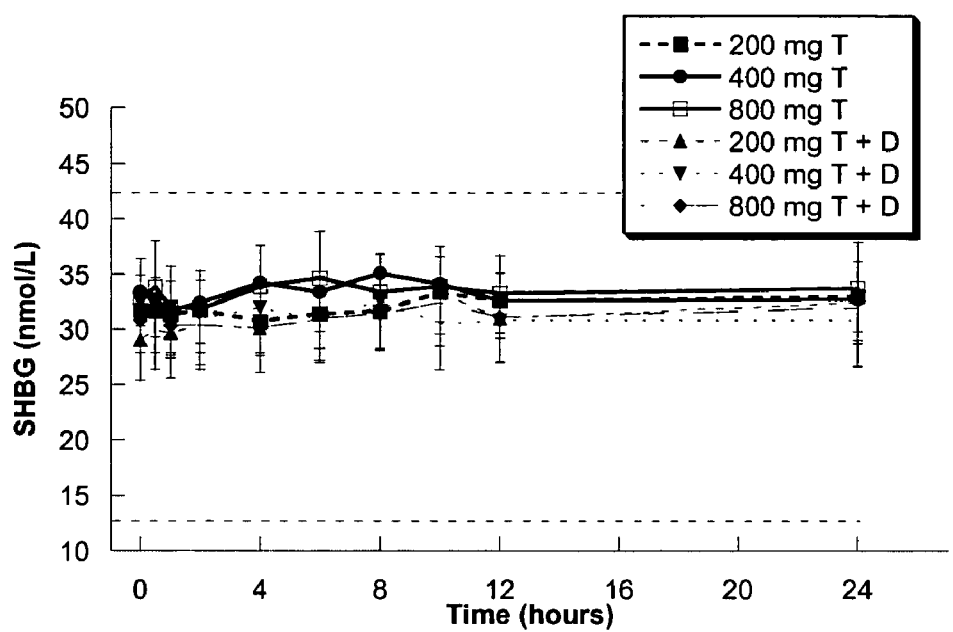

Serum SHBG: Serum SHBG did not change significantly after administration of acyline or with oral administration of testosterone or testosterone enanthate in oil either with or without concomitant dutasteride administration. (FIG. 10).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes to the extent not inconsistent to the present disclosures.

What is claimed is:

1. A method of providing androgen therapy to a human subject, said method comprising:
   administering to the subject a modulator of testosterone bioavailability, wherein the modulator is a compound having the formula:

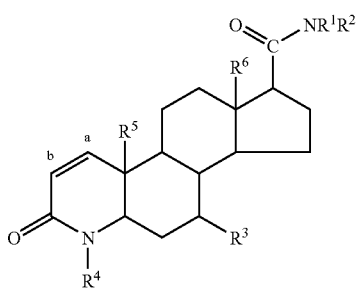

Formula I wherein $R^1$ is hydrogen or lower alkyl, and $R^2$ is optionally substituted alkyl or optionally substituted phenyl wherein the phenyl has 0, 1, 2, or 3 substituents selected from the group consisting of lower alkyl, halogen, and trifluoromethyl, and $R^3$, $R^4$, $R^5$, and $R^6$ are independently selected from the group consisting of hydrogen and optionally substituted lower alkyl, and the bond between adjacent carbon atom a and carbon atom b can optionally be replaced by a single bond in which the adjacent carbons are independently substituted with hydrogen or methyl, and the pharmaceutically acceptable salts thereof; and
   orally administering in an oil vehicle-an androgen selected from the group consisting of testosterone, testosterone esters, and testosterone precursors.

2. The method of claim 1, wherein the modulator is finasteride or dutasteride or a pharmaceutically acceptable salt thereof.

3. The method of claim 2, wherein the modulator is dutasteride.

4. The method of claim 2, wherein the modulator is finasteride.

5. The method of claim 1, wherein the androgen is testosterone or a testosterone ester.

6. The method of claim 2, wherein the androgen is selected from the group consisting of testosterone, testosterone propionate, testosterone enanthate, testosterone cypionate, testosterone undecanoate.

7. The method of claim 1, wherein said oil vehicle comprises a mineral oil.

8. The method of claim 1, wherein said oil vehicle comprises a vegetable oil or a fish oil.

9. The method of claim 1, wherein said modulator and said androgen are administered at or about the same time.

10. The method of claim 1, wherein the modulator is administered before the androgen.

11. The method of claim 1, wherein the modulator is administered after the androgen.

12. The method of claim 1, wherein the modulator and androgen are administered together.

13. The method of claim 1, wherein the subject is a male with hypogonadism.

14. The method of claim 1, wherein the subject is a male with testosterone deficiency.

15. The method of claim 1, wherein the subject is a male with a total serum testosterone level below 12 nmol/liter.

16. The method of claim 14, wherein the subject is male and the androgen is testosterone or a testosterone ester and the androgen is administered in an amount from 25 mg to 800 mg per day and the modulator is administered in an amount capable of increasing the bioavailability of the testosterone or testosterone ester by at least 30%.

17. The method of claim 16, wherein the androgen is administered in an amount from about 100 to 400 mg per day.

18. The method of claim 16, wherein the androgen is administered in an amount from 50 to 200 mg per day.

19. The method of claim 16, wherein the androgen is administered in an amount from 25 to 100 mg per day.

20. The method of claim 16, wherein the modulator is dutasteride or finasteride.

21. The method of claim 1, wherein the subject is male adult or male adolescent.

22. The method of claim 1, wherein the subject is a female adult or female adolescent.

23. The method of claim 1, wherein the testosterone precursor is 4-androstenediol or 4-androstenedione.

24. A method of enhancing the bioavailability of testosterone in a subject who is to receive an oral dose of an androgen formulated in an oil vehicle said method comprising administering to the subject a modulator of testosterone bioavailability of the formula:

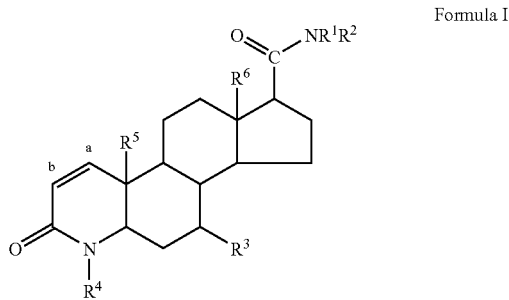

Formula I wherein $R^1$ is hydrogen or lower alkyl, and $R^2$ is optionally substituted alkyl or optionally substituted phenyl wherein the phenyl has 0, 1, 2, or 3 substituents selected from the group consisting of lower alkyl, halogen, and trifluoromethyl, and $R^3$, $R^4$, $R^{5\prime\prime}$, and $R^6$ are independently selected from the group consisting of hydrogen and optionally substituted lower alkyl, and the bond between adjacent carbon atom a and carbon atom b can optionally be replaced by a single bond in which the adjacent carbons are independently substituted with hydrogen or methyl, and the pharmaceutically acceptable salts thereof;
   and wherein the androgen is selected from the group consisting of testosterone, testosterone esters, and testosterone precursors.

25. The method of claim 24, wherein the modulator is finasteride or dutasteride and the androgen is testosterone or a testosterone ester.

26. A pharmaceutical composition comprising an oil vehicle containing 1) testosterone, testosterone ester or a testosterone precursor and 2) a modulator of testosterone bioavailability of the formula:

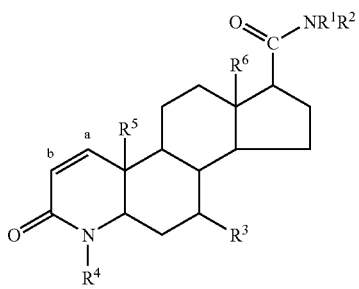

Formula I wherein $R^1$ is hydrogen or lower alkyl, and $R^2$ is optionally substituted alkyl or optionally substituted phenyl wherein the phenyl has 0, 1, 2, or 3 substituents selected from the group consisting of lower alkyl, halogen, and trifluoromethyl, and $R^3$, $R^4$, $R^5$, and $R^6$ are independently selected from the group consisting of hydrogen and optionally substituted lower alkyl, and the bond between adjacent carbon atom a and carbon atom can optionally be replaced by a single bond in which the adjacent carbons are independently substituted with hydrogen or methyl, and the pharmaceutically acceptable salts thereof; and wherein the composition is in an oral formulation.

27. The composition of claim 26 wherein the modulator is finasteride or dutasteride and the androgen is testosterone or a testosterone ester and the composition is encapsulated.

* * * * *